US012708360B2

(12) United States Patent
Marchand et al.

(10) Patent No.: US 12,708,360 B2
(45) Date of Patent: Aug. 18, 2026

(54) FILAMENTARY FIXATION DEVICE

(71) Applicant: Howmedica Osteonics Corp., Mahwah, NJ (US)

(72) Inventors: José Raúl Marchand, San Juan, PR (US); Ryan E. Yearsley, Denver, CO (US); Kyle Craig Pilgeram, San Jose, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 164 days.

(21) Appl. No.: 18/519,835

(22) Filed: Nov. 27, 2023

(65) Prior Publication Data

US 2024/0090891 A1 Mar. 21, 2024

Related U.S. Application Data

(63) Continuation of application No. 16/593,378, filed on Oct. 4, 2019, now Pat. No. 11,844,508, which is a (Continued)

(51) Int. Cl.
*A61B 17/04* (2006.01)

(52) U.S. Cl.
CPC .... *A61B 17/0401* (2013.01); *A61B 2017/042* (2013.01); *A61B 2017/0445* (2013.01); *A61B 2017/0459* (2013.01)

(58) Field of Classification Search
CPC .......... A61B 17/0401; A61B 17/06166; A61B 2017/0403; A61B 2017/0404;

(Continued)

(56) References Cited

U.S. PATENT DOCUMENTS 749,624 A 1/1904 McCullough
919,138 A 4/1909 Drake et al.

(Continued)

FOREIGN PATENT DOCUMENTS

CA 2713309 A1 2/2011
DE 3131496 A1 2/1983

(Continued)

OTHER PUBLICATIONS

Australian Examination Report for Application No. 2013202699 dated Feb. 21, 2014.

(Continued)

*Primary Examiner* — Dianne Dornbusch
(74) *Attorney, Agent, or Firm* — Foley & Lardner LLP

(57) ABSTRACT

In one embodiment of the present invention, a fixation device including a sleeve member including an interior and an exterior surface along a length defined between a first end and a second end, and at least two openings positioned along the length and extending from the interior and through the exterior surface; and a filament including a first free end and a second free end and a length therebetween, the filament positioned relative to the sleeve member such that the free ends extend from the sleeve member at the first and second ends of the sleeve member, the filament being disposed inside the interior from the first end to a first opening, outside the sleeve member from the first opening to a second opening, and inside the interior from the second opening to the second end of the sleeve member.

20 Claims, 18 Drawing Sheets

Related U.S. Application Data continuation of application No. 15/243,183, filed on Aug. 22, 2016, now Pat. No. 10,448,944, which is a continuation of application No. 13/303,849, filed on Nov. 23, 2011, now Pat. No. 9,445,803.

(58) Field of Classification Search
CPC .... A61B 2017/0406; A61B 2017/0408; A61B 2017/0414; A61B 2017/0417; A61B 2017/0419; A61B 2017/042; A61B 2017/0438; A61B 2017/0445; A61B 2017/06185
See application file for complete search history.

(56) References Cited

U.S. PATENT DOCUMENTS 1,308,798 A 7/1919 Masland
1,624,530 A 4/1927 Caruso
2,073,903 A 3/1937 O'Neil
2,250,434 A 7/1941 Dugaw
2,267,925 A 12/1941 Johnston
2,382,019 A 8/1945 Miller
2,416,260 A 2/1947 Karle
2,461,947 A 2/1949 Weber
2,494,229 A 1/1950 Collison
2,515,365 A 7/1950 Zublin
2,547,571 A 4/1951 Ettinger
2,579,192 A 12/1951 Kohl
2,773,672 A 12/1956 Holmes et al.
2,808,055 A 10/1957 Thayer
2,808,632 A 10/1957 Cline
2,833,284 A 5/1958 Springer
3,384,085 A 5/1968 Hall
3,407,889 A 10/1968 Hjalsten et al.
3,461,875 A 8/1969 Hall
3,554,192 A 1/1971 Isberner
3,566,739 A 3/1971 Lebar
3,580,256 A 5/1971 Wilkinson et al.
3,608,095 A 9/1971 Barry
3,659,597 A 5/1972 Wolfers
3,708,883 A 1/1973 Flander
3,750,671 A 8/1973 Hedrick
3,810,456 A 5/1974 Karman
3,845,772 A 11/1974 Smith
3,867,932 A 2/1975 Huene
3,892,232 A 7/1975 Neufeld
3,976,079 A 8/1976 Samuels et al.
3,981,051 A 9/1976 Brumlik
4,212,569 A 7/1980 Andersson et al.
4,265,231 A 5/1981 Scheller, Jr. et al.
4,328,839 A 5/1982 Lyons et al.
4,408,938 A 10/1983 Maguire
4,483,562 A 11/1984 Schoolman
4,484,570 A 11/1984 Sutter et al.
4,489,446 A 12/1984 Reed
4,492,226 A 1/1985 Belykh et al.
4,541,423 A 9/1985 Barber
4,590,928 A 5/1986 Hunt et al.
4,594,033 A 6/1986 Peetz et al.
4,605,347 A 8/1986 Jodock et al.
4,605,414 A 8/1986 Czajka
4,608,972 A 9/1986 Small
4,611,515 A 9/1986 Marbourg, Jr.
4,632,100 A 12/1986 Somers et al.
4,635,738 A 1/1987 Schillinger et al.
4,646,738 A 3/1987 Trott
4,706,659 A 11/1987 Matthews et al.
4,708,132 A 11/1987 Silvestrini
4,728,231 A 3/1988 Kunimori et al.
4,741,330 A 5/1988 Hayhurst
4,748,872 A 6/1988 Brown
4,751,922 A 6/1988 DiPietropolo
4,778,468 A 10/1988 Hunt et al.
4,779,616 A 10/1988 Johnson
4,781,182 A 11/1988 Purnell et al.
4,823,780 A 4/1989 Odensten et al.
4,842,451 A 6/1989 Dugger
4,863,471 A 9/1989 Mansat
4,870,957 A 10/1989 Goble et al.
4,871,289 A 10/1989 Choiniere
4,872,451 A 10/1989 Moore et al.
4,898,505 A 2/1990 Froehlich
4,927,421 A 5/1990 Goble et al.
4,946,462 A 8/1990 Watanabe
5,002,546 A 3/1991 Romano
5,007,911 A 4/1991 Baker
5,021,059 A 6/1991 Kensey et al.
5,030,219 A 7/1991 Matsen, III et al.
5,037,422 A 8/1991 Hayhurst et al.
5,037,423 A 8/1991 Kenna
5,046,513 A 9/1991 Gatturna et al.
5,061,277 A 10/1991 Carpentier et al.
5,064,431 A 11/1991 Gilbertson et al.
5,122,134 A 6/1992 Borzone et al.
5,123,914 A 6/1992 Cope
5,133,720 A 7/1992 Greenberg
5,139,520 A 8/1992 Rosenberg
5,141,520 A 8/1992 Goble et al.
5,163,940 A 11/1992 Bourque
5,165,494 A 11/1992 Barr
5,176,682 A 1/1993 Chow
5,186,268 A 2/1993 Clegg
5,190,548 A 3/1993 Davis
5,203,595 A 4/1993 Borzone et al.
5,203,787 A 4/1993 Noblitt et al.
5,207,679 A 5/1993 Li
5,209,753 A 5/1993 Biedermann et al.
RE34,293 E 6/1993 Goble et al.
5,224,946 A 7/1993 Hayhurst et al.
5,226,426 A 7/1993 Yoon
5,234,435 A 8/1993 Seagrave, Jr.
5,236,445 A 8/1993 Hayhurst et al.
5,259,846 A 11/1993 Granger et al.
5,268,001 A 12/1993 Nicholson et al.
5,269,785 A 12/1993 Bonutti
5,269,809 A 12/1993 Hayhurst et al.
5,273,380 A 12/1993 Musacchia
5,300,077 A 4/1994 Howell
5,314,429 A 5/1994 Goble
5,320,115 A 6/1994 Kenna
5,320,626 A 6/1994 Schmieding
5,324,308 A 6/1994 Pierce
5,330,442 A 7/1994 Green et al.
5,330,468 A 7/1994 Burkhart
5,336,240 A 8/1994 Metzler et al.
5,342,376 A 8/1994 Ruff
5,350,383 A 9/1994 Schmieding et al.
RE34,762 E 10/1994 Goble et al.
5,354,298 A 10/1994 Lee et al.
5,364,407 A 11/1994 Poll
5,374,269 A 12/1994 Rosenberg
5,380,334 A 1/1995 Torrie et al.
5,383,905 A 1/1995 Golds et al.
5,385,567 A 1/1995 Goble
5,391,170 A 2/1995 McGuire et al.
5,391,171 A 2/1995 Schmieding
RE34,871 E 3/1995 McGuire et al.
5,395,188 A 3/1995 Bailey et al.
5,403,317 A 4/1995 Bonutti
5,403,348 A 4/1995 Bonutti
5,405,352 A 4/1995 Weston
5,405,359 A 4/1995 Pierce
5,409,494 A 4/1995 Morgan
5,411,523 A 5/1995 Goble
5,417,691 A 5/1995 Hayhurst
5,417,712 A 5/1995 Whittaker et al.
5,423,824 A 6/1995 Akerfeldt et al.
5,423,860 A 6/1995 Lizardi et al.
5,437,630 A 8/1995 Daniel et al.
5,437,675 A 8/1995 Wilson
5,437,677 A 8/1995 Shearer et al.
5,441,502 A 8/1995 Bartlett
5,443,482 A 8/1995 Stone et al.
5,458,604 A 10/1995 Schmieding

(56) References Cited

U.S. PATENT DOCUMENTS 5,464,407 A 11/1995 McGuire
5,464,425 A 11/1995 Skiba
5,464,426 A 11/1995 Bonutti
5,464,427 A 11/1995 Curtis et al.
5,466,243 A 11/1995 Schmieding et al.
5,472,452 A 12/1995 Trott
5,480,403 A 1/1996 Lee et al.
5,486,197 A 1/1996 Le et al.
5,488,761 A 2/1996 Leone
5,489,210 A 2/1996 Hanosh
5,496,348 A 3/1996 Bonutti
5,499,991 A 3/1996 Garman et al.
5,501,683 A 3/1996 Trott
5,501,692 A 3/1996 Riza
5,501,695 A 3/1996 Anspach, Jr. et al.
5,505,736 A 4/1996 Reimels et al.
5,514,159 A 5/1996 Matula et al.
5,520,693 A 5/1996 McGuire et al.
5,520,700 A 5/1996 Beyar et al.
5,522,844 A 6/1996 Johnson
5,522,845 A 6/1996 Wenstrom, Jr.
5,522,846 A 6/1996 Bonutti
5,527,316 A 6/1996 Stone et al.
5,527,343 A 6/1996 Bonutti
5,529,580 A 6/1996 Kusunoki et al.
5,531,759 A 7/1996 Kensey et al.
5,534,012 A 7/1996 Bonutti
5,540,703 A 7/1996 Barker, Jr. et al.
5,545,178 A 8/1996 Kensey et al.
5,545,180 A 8/1996 Le et al.
5,548,862 A 8/1996 Curtis
5,562,683 A 10/1996 Chan
5,562,687 A 10/1996 Chan
5,569,269 A 10/1996 Hart et al.
5,569,306 A 10/1996 Thal
5,570,706 A 11/1996 Howell
5,571,111 A 11/1996 Aboczky
5,571,139 A 11/1996 Jenkins, Jr.
5,573,537 A 11/1996 Rogozinski
5,573,542 A 11/1996 Stevens
5,575,819 A 11/1996 Amis
5,584,617 A 12/1996 Houser
5,584,695 A 12/1996 Lal Sachdeva et al.
5,584,835 A 12/1996 Greenfield
5,601,550 A 2/1997 Esser
5,601,557 A 2/1997 Hayhurst
5,601,558 A 2/1997 Torrie et al.
5,601,561 A 2/1997 Terry et al.
5,611,515 A 3/1997 Benderev et al.
5,618,314 A 4/1997 Harwin et al.
5,630,824 A 5/1997 Hart
5,632,748 A 5/1997 Beck, Jr. et al.
5,643,292 A 7/1997 Hart
5,643,321 A 7/1997 McDevitt
5,645,545 A 7/1997 Bryant
5,645,589 A 7/1997 Li
5,647,874 A 7/1997 Hayhurst
5,649,963 A 7/1997 McDevitt
5,658,289 A 8/1997 Boucher et al.
5,658,313 A 8/1997 Thal
5,662,654 A 9/1997 Thompson
5,662,658 A 9/1997 Wenstrom, Jr.
5,664,914 A 9/1997 Taniguchi
5,665,110 A 9/1997 Chervitz et al.
5,665,111 A 9/1997 Ray et al.
5,665,112 A 9/1997 That
5,667,509 A 9/1997 Westin
5,671,695 A 9/1997 Schroeder
5,674,279 A 10/1997 Wright et al.
5,681,315 A 10/1997 Szabo
5,681,320 A 10/1997 McGuire
5,681,333 A 10/1997 Burkhart et al.
5,681,352 A 10/1997 Clancy, III et al.
5,683,401 A 11/1997 Schmieding et al.
5,683,418 A 11/1997 Luscombe et al.
5,683,419 A 11/1997 Thal
5,690,649 A 11/1997 Li
5,690,676 A 11/1997 DiPoto et al.
5,690,677 A 11/1997 Schmieding et al.
5,695,513 A 12/1997 Johnson et al.
5,699,657 A 12/1997 Paulson
5,702,215 A 12/1997 Li
5,702,397 A 12/1997 Goble et al.
5,702,422 A 12/1997 Stone
5,707,374 A 1/1998 Schmidt
5,707,395 A 1/1998 Li
5,709,708 A 1/1998 Thal
5,713,905 A 2/1998 Goble et al.
5,716,368 A 2/1998 de la Torre et al.
5,716,397 A 2/1998 Myers
5,718,717 A 2/1998 Bonutti
5,720,765 A 2/1998 Thai
5,725,529 A 3/1998 Nicholson et al.
5,725,530 A 3/1998 Popken
5,725,541 A 3/1998 Anspach, III et al.
5,725,557 A 3/1998 Gatturna et al.
5,728,136 A 3/1998 Thal
5,732,606 A 3/1998 Chiang
5,733,306 A 3/1998 Bonutti
5,733,307 A 3/1998 Dinsdale
5,741,300 A 4/1998 Li
5,746,752 A 5/1998 Burkhart
5,746,753 A 5/1998 Sullivan et al.
5,749,899 A 5/1998 Bardin et al.
5,755,724 A 5/1998 Yoon
5,755,728 A 5/1998 Maki
5,755,731 A 5/1998 Grinberg
5,759,185 A 6/1998 Grinberg
5,766,221 A 6/1998 Benderev et al.
5,782,862 A 7/1998 Bonutti
5,782,863 A 7/1998 Bartlett
5,782,864 A 7/1998 Lizardi
5,782,866 A 7/1998 Wenstrom, Jr.
5,788,699 A 8/1998 Bobst et al.
5,791,899 A 8/1998 Sachdeva et al.
5,797,918 A 8/1998 McGuire et al.
5,797,963 A 8/1998 McDevitt
5,810,825 A 9/1998 Huebner
5,814,056 A 9/1998 Prosst et al.
5,814,071 A 9/1998 McDevitt et al.
5,814,072 A 9/1998 Bonutti
5,814,073 A 9/1998 Bonutti
5,820,464 A 10/1998 Parlato
5,836,953 A 11/1998 Yoon
5,843,127 A 12/1998 Li
5,845,645 A 12/1998 Bonutti
5,849,004 A 12/1998 Bramlet
5,851,208 A 12/1998 Trott
5,885,294 A 3/1999 Pedlick et al.
5,888,034 A 3/1999 Greenberg
5,891,168 A 4/1999 That
5,895,179 A 4/1999 Gschwend et al.
5,897,574 A 4/1999 Bonutti
5,906,624 A 5/1999 Wenstrom, Jr.
5,906,626 A 5/1999 Carrillo
5,908,423 A 6/1999 Kashuba et al.
5,910,148 A 6/1999 Reimels et al.
5,911,721 A 6/1999 Nicholson et al.
5,921,986 A 7/1999 Bonutti
5,928,244 A 7/1999 Tovey et al.
5,935,129 A 8/1999 McDevitt et al.
5,935,134 A 8/1999 Pedlick et al.
5,935,149 A 8/1999 Ek
5,941,139 A 8/1999 Vodehnal
5,941,883 A 8/1999 Sklar
5,947,659 A 9/1999 Mays
5,948,000 A 9/1999 Larsen et al.
5,948,001 A 9/1999 Larsen
5,948,002 A 9/1999 Bonutti
5,951,559 A 9/1999 Burkhart
5,954,747 A 9/1999 Clark
5,957,953 A 9/1999 DiPoto et al.
5,961,538 A 10/1999 Pedlick et al.
5,968,044 A 10/1999 Nicholson et al.

(56) References Cited

U.S. PATENT DOCUMENTS 5,968,078 A 10/1999 Grotz
5,970,697 A 10/1999 Jacobs et al.
5,980,539 A 11/1999 Kontos
5,980,558 A 11/1999 Wiley
5,980,559 A 11/1999 Bonutti
5,989,252 A 11/1999 Fumex
5,993,451 A 11/1999 Burkhart
5,993,459 A 11/1999 Larsen et al.
5,997,541 A 12/1999 Schenk
6,007,566 A 12/1999 Wenstrom, Jr.
6,007,567 A 12/1999 Bonutti
6,010,514 A 1/2000 Burney et al.
6,010,515 A 1/2000 Swain et al.
6,010,525 A 1/2000 Bonutti et al.
6,019,767 A 2/2000 Howell
6,022,360 A 2/2000 Reimels et al.
6,024,758 A 2/2000 Thal
6,030,406 A 2/2000 Davis et al.
6,041,485 A 3/2000 Pedlick et al.
6,045,573 A 4/2000 Wenstrom, Jr. et al.
6,045,574 A 4/2000 Thai
6,053,922 A 4/2000 Krause et al.
6,056,772 A 5/2000 Bonutti
6,068,642 A 5/2000 Johnson et al.
6,077,277 A 6/2000 Mollenauer et al.
6,077,292 A 6/2000 Bonutti
6,083,244 A 7/2000 Lubbers et al.
6,083,522 A 7/2000 Chu et al.
6,086,608 A 7/2000 Ek et al.
6,099,538 A 8/2000 Moses et al.
6,099,547 A 8/2000 Gellman et al.
6,117,144 A 9/2000 Nobles et al.
6,120,511 A 9/2000 Chan
6,143,017 A 11/2000 Thal
6,146,385 A 11/2000 Torrie et al.
6,149,669 A 11/2000 Li
6,152,949 A 11/2000 Bonutti
6,156,039 A 12/2000 Thal
6,156,056 A 12/2000 Kearns et al.
6,159,234 A 12/2000 Bonutti et al.
6,183,461 B1 2/2001 Matsuura et al.
6,187,011 B1 2/2001 Torrie
6,189,422 B1 2/2001 Stihl
6,200,329 B1 3/2001 Fung et al.
6,210,415 B1 4/2001 Bester
6,221,107 B1 4/2001 Steiner et al.
6,224,608 B1 5/2001 Ciccolella et al.
6,231,592 B1 5/2001 Bonutti et al.
6,241,732 B1 6/2001 Overaker et al.
6,245,081 B1 6/2001 Bowman et al.
6,245,082 B1 6/2001 Gellman et al.
6,254,604 B1 7/2001 Howell
6,258,093 B1 7/2001 Edwards et al.
6,270,501 B1 8/2001 Freiberg et al.
6,296,659 B1 10/2001 Foerster
6,306,138 B1 10/2001 Clark et al.
6,306,159 B1 10/2001 Schwartz et al.
6,312,432 B1 11/2001 Leppelmeier
6,312,438 B1 11/2001 Adams
6,312,448 B1 11/2001 Bonutti
6,319,252 B1 11/2001 McDevitt et al.
6,319,269 B1 11/2001 Li
6,343,482 B1 2/2002 Endo et al.
6,352,538 B2 3/2002 McGuire et al.
6,358,253 B1 3/2002 Torrie et al.
6,364,886 B1 4/2002 Sklar
6,383,188 B2 5/2002 Kuslich et al.
6,402,781 B1 6/2002 Langberg et al.
6,416,517 B2 7/2002 Harder et al.
6,419,678 B1 7/2002 Asfora
6,419,684 B1 7/2002 Heisler et al.
6,431,801 B2 8/2002 Vasudeva et al.
6,436,100 B1 8/2002 Berger
6,436,124 B1 8/2002 Anderson et al.
6,440,138 B1 8/2002 Reiley et al.
6,440,141 B1 8/2002 Philippon
6,447,518 B1 9/2002 Krause et al.
6,464,713 B2 10/2002 Bonutti
6,474,425 B1 11/2002 Truax et al.
6,475,230 B1 11/2002 Bonutti et al.
6,478,800 B1 11/2002 Fraser et al.
6,485,504 B1 11/2002 Johnson et al.
6,494,272 B1 12/2002 Eppink et al.
6,500,195 B2 12/2002 Bonutti
RE37,963 E 1/2003 Thal
6,506,190 B1 1/2003 Walshe
6,508,830 B2 1/2003 Steiner
6,511,498 B1 1/2003 Fumex
6,517,578 B2 2/2003 Hein
6,517,579 B1 2/2003 Paulos et al.
6,520,980 B1 2/2003 Foerster
6,524,316 B1 2/2003 Nicholson et al.
6,527,794 B1 3/2003 McDevitt et al.
6,527,795 B1 3/2003 Lizardi
6,544,281 B2 4/2003 ElAttrache et al.
6,547,800 B2 4/2003 Foerster et al.
6,547,807 B2 4/2003 Chan et al.
6,558,386 B1 5/2003 Cragg
6,558,390 B2 5/2003 Cragg
6,562,071 B2 5/2003 Jarvinen
6,569,187 B1 5/2003 Bonutti et al.
6,572,635 B1 6/2003 Bonutti
6,575,976 B2 6/2003 Grafton
6,575,979 B1 6/2003 Cragg
6,575,987 B2 6/2003 Gellman et al.
6,582,453 B1 6/2003 Tran et al.
6,585,730 B1 7/2003 Foerster
6,599,310 B2 7/2003 Leung et al.
6,610,080 B2 8/2003 Morgan
6,620,166 B1 9/2003 Wenstrom, Jr. et al.
6,629,984 B1 10/2003 Chan
6,635,073 B2 10/2003 Bonutti
6,638,279 B2 10/2003 Bonutti
6,638,283 B2 10/2003 Thal
6,641,596 B1 11/2003 Lizardi
6,641,597 B2 11/2003 Burkhart et al.
6,652,450 B2 11/2003 Neisz et al.
6,660,008 B1 12/2003 Foerster et al.
6,660,023 B2 12/2003 McDevitt et al.
6,673,094 B1 1/2004 McDevitt et al.
6,692,516 B2 2/2004 West, Jr. et al.
6,712,822 B2 3/2004 Re et al.
6,716,234 B2 4/2004 Grafton et al.
6,730,092 B2 5/2004 Songer
6,733,506 B1 5/2004 McDevitt et al.
6,740,090 B1 5/2004 Cragg et al.
6,746,451 B2 6/2004 Middleton et al.
6,746,457 B2 6/2004 Dana et al.
6,752,814 B2 6/2004 Gellman et al.
6,770,073 B2 8/2004 McDevitt et al.
6,770,076 B2 8/2004 Foerster
6,773,450 B2 8/2004 Leung et al.
6,780,188 B2 8/2004 Clark et al.
6,780,198 B1 8/2004 Gregoire et al.
6,783,533 B2 8/2004 Green et al.
6,790,210 B1 9/2004 Cragg et al.
6,805,697 B1 10/2004 Helm et al.
6,814,741 B2 11/2004 Bowman et al.
6,824,552 B2 11/2004 Robison et al.
6,830,570 B1 12/2004 Frey et al.
6,848,152 B2 2/2005 Genova et al.
6,855,157 B2 2/2005 Foerster et al.
6,863,672 B2 3/2005 Reiley et al.
6,874,978 B2 4/2005 Gongola
6,878,150 B1 4/2005 McGuire et al.
6,887,259 B2 5/2005 Lizardi
6,893,445 B1 5/2005 Revie et al.
6,899,716 B2 5/2005 Cragg
6,921,403 B2 7/2005 Cragg et al.
6,923,811 B1 8/2005 Carl et al.
6,923,814 B1 8/2005 Hildebrand et al.
6,932,834 B2 8/2005 Lizardi et al.
6,936,052 B2 8/2005 Gellman et al.
6,942,666 B2 9/2005 Overaker et al.

(56) References Cited

U.S. PATENT DOCUMENTS 6,955,683 B2 10/2005 Bonutti
6,960,214 B2 11/2005 Burkinshaw
6,984,241 B2 1/2006 Lubbers et al.
6,986,781 B2 1/2006 Smith
6,991,636 B2 1/2006 Rose
6,994,719 B2 2/2006 Grafton
6,994,725 B1 2/2006 Goble
6,995,683 B2 2/2006 Smithson et al.
7,008,431 B2 3/2006 Simonson
7,018,144 B2 3/2006 Sasagawa et al.
7,025,770 B2 4/2006 McGuire et al.
7,029,479 B2 4/2006 Tallarida et al.
7,029,490 B2 4/2006 Grafton et al.
7,033,380 B2 4/2006 Schwartz et al.
7,037,324 B2 5/2006 Martinek
7,041,107 B2 5/2006 Pohjonen et al.
7,041,120 B2 5/2006 Li et al.
7,048,754 B2 5/2006 Martin et al.
7,048,755 B2 5/2006 Bonutti et al.
7,056,331 B2 6/2006 Kaplan et al.
7,060,073 B2 6/2006 Frey et al.
7,067,132 B2 6/2006 Grabstein et al.
7,074,203 B1 7/2006 Johanson et al.
7,077,863 B2 7/2006 Schmieding et al.
7,081,126 B2 7/2006 McDevitt et al.
7,083,638 B2 8/2006 Foerster
7,087,058 B2 8/2006 Cragg
7,087,073 B2 8/2006 Bonutti
7,090,690 B2 8/2006 Foerster et al.
7,144,415 B2 12/2006 Del Rio et al.
7,160,314 B2 1/2007 Sgro et al.
7,204,839 B2 4/2007 Dreyfuss et al.
7,217,279 B2 5/2007 Reese
7,217,290 B2 5/2007 Bonutti
7,225,512 B2 6/2007 Genova et al.
7,226,469 B2 6/2007 Benavitz et al.
7,235,091 B2 6/2007 Thornes
7,235,100 B2 6/2007 Martinek
7,241,297 B2 7/2007 Shaolian et al.
7,258,692 B2 8/2007 Thelen et al.
7,261,016 B2 8/2007 Miller
7,285,124 B2 10/2007 Foerster
7,309,338 B2 12/2007 Cragg
7,309,346 B2 12/2007 Martinek
7,326,215 B2 2/2008 Myers et al.
7,329,272 B2 2/2008 Burkhart et al.
7,331,263 B2 2/2008 Erickson et al.
7,371,253 B2 5/2008 Leung et al.
7,381,213 B2 6/2008 Lizardi
7,488,322 B2 2/2009 Brunnett et al.
7,488,329 B2 2/2009 Thelen et al.
7,494,490 B2 2/2009 Justin
7,500,977 B2 3/2009 Assell et al.
7,503,920 B2 3/2009 Siegal
7,507,200 B2 3/2009 Okada
7,517,357 B2 4/2009 Abrams et al.
7,520,898 B2 4/2009 Re et al.
7,556,640 B2 7/2009 Foerster
7,563,266 B2 7/2009 Camino et al.
7,578,836 B2 8/2009 Justin et al.
7,585,300 B2 9/2009 Cha
7,601,155 B2 10/2009 Petersen
7,601,165 B2 10/2009 Stone
7,604,636 B1 10/2009 Walters et al.
7,608,098 B1 10/2009 Stone et al.
7,611,521 B2 11/2009 Lubbers et al.
7,621,912 B2 11/2009 Harms et al.
7,621,940 B2 11/2009 Harms et al.
7,624,487 B2 12/2009 Trull et al.
7,637,926 B2 12/2009 Foerster et al.
7,651,509 B2 1/2010 Bojarski et al.
7,651,515 B2 1/2010 Mack et al.
7,658,751 B2 2/2010 Stone et al.
7,662,171 B2 2/2010 West, Jr. et al.
7,666,189 B2 2/2010 Gerber et al.
7,674,274 B2 3/2010 Foerster et al.
7,674,276 B2 3/2010 Stone et al.
7,678,134 B2 3/2010 Schmieding et al.
7,682,374 B2 3/2010 Foerster et al.
7,695,494 B2 4/2010 Foerster
7,704,262 B2 4/2010 Bellafiore et al.
7,713,286 B2 5/2010 Singhatat
7,749,250 B2 7/2010 Stone et al.
7,776,049 B1 8/2010 Curran et al.
7,780,701 B1 8/2010 Meridew et al.
7,794,484 B2 9/2010 Stone et al.
7,803,173 B2 9/2010 Burkhart et al.
7,828,820 B2 11/2010 Stone et al.
7,837,710 B2 11/2010 Lombardo et al.
7,842,050 B2 11/2010 Diduch et al.
7,846,167 B2 12/2010 Garcia et al.
7,857,829 B2 12/2010 Kaplan et al.
7,857,830 B2 12/2010 Stone et al.
7,867,264 B2 1/2011 McDevitt et al.
7,875,057 B2 1/2011 Cook et al.
7,875,058 B2 1/2011 Holmes, Jr.
7,879,037 B2 2/2011 Brunnett et al.
7,892,235 B2 2/2011 Ellis
7,892,256 B2 2/2011 Grafton et al.
7,896,907 B2 3/2011 McDevitt et al.
7,901,431 B2 3/2011 Shurnas
7,905,903 B2 3/2011 Stone et al.
7,905,904 B2 3/2011 Stone et al.
7,909,547 B2 3/2011 Jordan et al.
7,909,851 B2 3/2011 Stone et al.
7,913,365 B2 3/2011 Genova et al.
7,914,539 B2 3/2011 Stone et al.
7,918,874 B2 4/2011 Siegal
7,938,847 B2 5/2011 Fanton et al.
7,959,650 B2 6/2011 Kaiser et al.
7,963,967 B1 6/2011 Woods
7,963,972 B2 6/2011 Foerster et al.
7,976,565 B1 7/2011 Meridew
7,981,117 B2 7/2011 Newton et al.
7,981,140 B2 7/2011 Burkhart
7,993,369 B2 8/2011 Dreyfuss
7,996,967 B2 8/2011 Genova et al.
7,996,968 B2 8/2011 Genova et al.
8,002,733 B2 8/2011 Kraft et al.
8,011,072 B2 9/2011 Genova et al.
8,015,678 B2 9/2011 Genova et al.
8,020,263 B2 9/2011 Genova et al.
8,028,387 B2 10/2011 Genova et al.
8,028,388 B2 10/2011 Genova et al.
8,029,537 B2 10/2011 West, Jr. et al.
8,032,996 B2 10/2011 Trull et al.
8,043,253 B2 10/2011 Kraft et al.
8,057,500 B2 11/2011 Mitusina
8,057,524 B2 11/2011 Meridew
8,066,718 B2 11/2011 Weisel et al.
8,070,750 B2 12/2011 Wenstrom, Jr. et al.
8,075,572 B2 12/2011 Stefanchik et al.
8,083,770 B2 12/2011 Ruff et al.
RE43,143 E 1/2012 Hayhurst
8,088,130 B2 1/2012 Kaiser et al.
8,100,940 B2 1/2012 Leung et al.
8,100,942 B1 1/2012 Green et al.
8,109,700 B2 2/2012 Jordan et al.
8,109,969 B1 2/2012 Green et al.
8,114,088 B2 2/2012 Miller
8,118,834 B1 2/2012 Goraltchouk et al.
8,118,835 B2 2/2012 Weisel et al.
8,118,836 B2 2/2012 Denham et al.
8,123,750 B2 2/2012 Norton et al.
8,128,640 B2 3/2012 Harris et al.
8,128,641 B2 3/2012 Wardle
8,128,658 B2 3/2012 Kaiser et al.
8,128,669 B2 3/2012 Bonutti
8,133,231 B2 3/2012 Martinek et al.
8,133,258 B2 3/2012 Foerster et al.
8,137,381 B2 3/2012 Foerster et al.
8,137,382 B2 3/2012 Denham et al.
8,137,383 B2 3/2012 West, Jr. et al.
8,147,514 B2 4/2012 Bonutti

(56) References Cited

U.S. PATENT DOCUMENTS 8,162,978 B2 4/2012 Lombardo et al.
8,162,997 B2 4/2012 Struhl
8,172,846 B2 5/2012 Brunnett et al.
8,216,273 B1 7/2012 Goraltchouk et al.
8,231,654 B2 7/2012 Kaiser et al.
8,231,674 B2 7/2012 Albertorio et al.
8,241,305 B2 8/2012 Stone
8,246,652 B2 8/2012 Ruff
8,267,959 B2 9/2012 Fallman
8,273,106 B2 9/2012 Stone et al.
8,292,921 B2 10/2012 Stone et al.
8,298,262 B2 10/2012 Stone et al.
8,298,291 B2 10/2012 Ewers et al.
8,303,604 B2 11/2012 Stone et al.
8,312,942 B2 11/2012 Ho et al.
8,317,825 B2 11/2012 Stone
8,337,525 B2 12/2012 Stone et al.
8,343,187 B2 1/2013 Lamson et al.
8,361,113 B2 1/2013 Stone et al.
8,366,713 B2 2/2013 Long et al.
8,394,129 B2 3/2013 Morgenstern Lopez et al.
8,398,678 B2 3/2013 Baker et al.
8,409,252 B2 4/2013 Lombardo et al.
8,409,253 B2 4/2013 Stone et al.
8,435,264 B2 5/2013 Sojka et al.
8,439,976 B2 5/2013 Albertorio et al.
8,444,672 B2 5/2013 Foerster
8,444,674 B2 5/2013 Kaplan
8,454,704 B2 6/2013 Frushell et al.
8,460,338 B2 6/2013 Goraltchouk et al.
8,460,340 B2 6/2013 Sojka et al.
8,460,379 B2 6/2013 Albertorio et al.
8,469,998 B2 6/2013 Sojka et al.
8,491,600 B2 7/2013 McDevitt et al.
8,512,340 B2 8/2013 Easley et al.
8,518,087 B2 8/2013 Lopez et al.
8,523,902 B2 9/2013 Heaven et al.
8,545,535 B2 10/2013 Hirotsuka et al.
8,545,536 B2 10/2013 Mayer et al.
8,556,911 B2 10/2013 Mehta et al.
8,562,645 B2 10/2013 Stone et al.
8,591,578 B2 11/2013 Albertorio et al.
8,597,333 B2 12/2013 Morgenstern Lopez et al.
8,613,756 B2 12/2013 Lizardi et al.
8,623,051 B2 1/2014 Bojarski et al.
8,632,568 B2 1/2014 Miller et al.
8,663,324 B2 3/2014 Schmieding et al.
8,801,800 B2 8/2014 Bagga et al.
8,814,905 B2 8/2014 Sengun et al.
8,821,543 B2 9/2014 Hernandez et al.
8,821,544 B2 9/2014 Sengun et al.
8,821,545 B2 9/2014 Sengun
8,834,543 B2 9/2014 McDevitt et al.
8,936,620 B2 1/2015 Kaiser et al.
8,986,345 B2 3/2015 Denham et al.
9,072,530 B2 7/2015 Mehta et al.
9,370,350 B2 6/2016 Norton
9,445,803 B2 9/2016 Marchand et al.
9,451,938 B2 9/2016 Overes et al.
10,292,694 B2 5/2019 Graul et al.
2001/0002436 A1 5/2001 Bowman et al.
2001/0027320 A1 10/2001 Sasso
2001/0049529 A1 12/2001 Cachia et al.
2002/0019635 A1 2/2002 Wenstrom et al.
2002/0040241 A1 4/2002 Jarvinen
2002/0052649 A1 5/2002 Greenhalgh
2002/0087166 A1 7/2002 Brock et al.
2002/0115999 A1 8/2002 McDevitt et al.
2002/0147456 A1 10/2002 Diduch et al.
2002/0183758 A1 12/2002 Middleton et al.
2002/0188301 A1 12/2002 Dallara et al.
2003/0004545 A1 1/2003 Burkhart et al.
2003/0032961 A1 2/2003 Pelo et al.
2003/0065361 A1 4/2003 Dreyfuss
2003/0139752 A1 7/2003 Pasricha et al.
2003/0167071 A1* 9/2003 Martin .............. A61B 17/0487 606/232
2003/0176919 A1 9/2003 Schmieding
2003/0191487 A1 10/2003 Robison et al.
2003/0195563 A1 10/2003 Foerster
2003/0195564 A1 10/2003 Tran et al.
2003/0195565 A1 10/2003 Bonutti
2003/0220646 A1 11/2003 Thelen et al.
2003/0233098 A1 12/2003 Markworth
2004/0010264 A1 1/2004 Acker et al.
2004/0010287 A1 1/2004 Bonutti
2004/0030346 A1 2/2004 Frey et al.
2004/0049194 A1 3/2004 Harvie et al.
2004/0060409 A1 4/2004 Leung et al.
2004/0073227 A1 4/2004 Dreyfuss et al.
2004/0073306 A1 4/2004 Eichhorn et al.
2004/0092933 A1 5/2004 Shaolian et al.
2004/0093031 A1 5/2004 Burkhart et al.
2004/0138706 A1 7/2004 Abrams et al.
2004/0147958 A1 7/2004 Lam et al.
2004/0149093 A1 8/2004 Tang
2004/0193168 A1 9/2004 Long et al.
2004/0193217 A1 9/2004 Lubbers et al.
2004/0208717 A1 10/2004 Greenhalgh
2004/0220573 A1 11/2004 McDevitt et al.
2004/0220593 A1 11/2004 Greenhalgh
2004/0249393 A1 12/2004 Weisel et al.
2004/0260300 A1 12/2004 Gorensek et al.
2004/0267277 A1 12/2004 Zannis et al.
2004/0267317 A1 12/2004 Higgins et al.
2005/0004644 A1 1/2005 Kelsch et al.
2005/0015153 A1 1/2005 Goble et al.
2005/0033362 A1 2/2005 Grafton
2005/0038427 A1 2/2005 Perriello et al.
2005/0049592 A1 3/2005 Keith et al.
2005/0049681 A1 3/2005 Greenhalgh et al.
2005/0070906 A1 3/2005 Clark et al.
2005/0075668 A1 4/2005 Lizardi
2005/0080400 A1 4/2005 Corcoran et al.
2005/0137600 A1 6/2005 Jacobs et al.
2005/0137601 A1 6/2005 Assell et al.
2005/0143741 A1 6/2005 Timmermans et al.
2005/0147478 A1 7/2005 Greenberg
2005/0149122 A1 7/2005 McDevitt et al.
2005/0171569 A1 8/2005 Girard et al.
2005/0177168 A1 8/2005 Brunnett et al.
2005/0187537 A1 8/2005 Loeb et al.
2005/0203527 A1 9/2005 Carrison et al.
2005/0228399 A1 10/2005 Kubo et al.
2005/0245932 A1 11/2005 Fanton et al.
2005/0251159 A1 11/2005 Ewers et al.
2005/0251208 A1* 11/2005 Elmer ................ A61B 17/0401 606/232
2005/0261604 A1 11/2005 Stephens et al.
2005/0277986 A1 12/2005 Foerster et al.
2005/0283156 A1 12/2005 Schmieding et al.
2005/0283171 A1 12/2005 Bellafiore et al.
2005/0288710 A1 12/2005 Fallin et al.
2006/0001518 A1 1/2006 Hayashi et al.
2006/0004369 A1 1/2006 Patel et al.
2006/0004410 A1* 1/2006 Nobis ................ A61B 17/0469 606/232
2006/0015108 A1 1/2006 Bonutti
2006/0015110 A1 1/2006 Pepper
2006/0030884 A1 2/2006 Yeung et al.
2006/0052788 A1 3/2006 Thelen et al.
2006/0074434 A1 4/2006 Wenstrom et al.
2006/0079904 A1 4/2006 Thal
2006/0081553 A1 4/2006 Patterson et al.
2006/0100631 A1 5/2006 Sullivan et al.
2006/0106423 A1 5/2006 Weisel et al.
2006/0155329 A1 7/2006 Grafton et al.
2006/0178748 A1 8/2006 Dinger et al.
2006/0189993 A1 8/2006 Stone
2006/0190042 A1 8/2006 Stone et al.
2006/0212055 A1 9/2006 Karabey et al.
2006/0217762 A1 9/2006 Maahs et al.
2006/0235413 A1 10/2006 Denham et al.
2006/0241675 A1 10/2006 Johnson et al.

(56) References Cited

U.S. PATENT DOCUMENTS

2006/0247641 A1 11/2006 Re et al.
2006/0247642 A1 11/2006 Stone et al.
2006/0265010 A1 11/2006 Paraschac et al.
2006/0282081 A1 12/2006 Fanton et al.
2006/0282082 A1 12/2006 Fanton et al.
2006/0282083 A1 12/2006 Fanton et al.
2006/0282085 A1 12/2006 Stone et al.
2006/0293689 A1 12/2006 Miller et al.
2007/0005068 A1 1/2007 Sklar
2007/0010843 A1 1/2007 Green
2007/0010857 A1* 1/2007 Sugimoto ........ A61B 17/00234 606/232
2007/0032800 A1* 2/2007 Ortiz .................... A61F 5/0086 606/148
2007/0060922 A1 3/2007 Dreyfuss
2007/0093840 A1 4/2007 Pacelli et al.
2007/0093858 A1 4/2007 Gambale et al.
2007/0112385 A1 5/2007 Conlon
2007/0156149 A1 7/2007 Fanton et al.
2007/0156150 A1 7/2007 Fanton et al.
2007/0156176 A1 7/2007 Fanton et al.
2007/0167950 A1 7/2007 Tauro et al.
2007/0185532 A1* 8/2007 Stone ................ A61B 17/0482 606/232
2007/0191853 A1 8/2007 Stone
2007/0203498 A1 8/2007 Gerber et al.
2007/0213734 A1 9/2007 Bleich et al.
2007/0213735 A1 9/2007 Saadat et al.
2007/0225721 A1 9/2007 Thelen et al.
2007/0233151 A1 10/2007 Chudik
2007/0255317 A1 11/2007 Fanton et al.
2007/0260259 A1 11/2007 Fanton et al.
2007/0270889 A1 11/2007 Conlon et al.
2007/0270907 A1 11/2007 Stokes et al.
2007/0276392 A1 11/2007 Beyar et al.
2007/0288023 A1 12/2007 Pellegrino et al.
2007/0288027 A1 12/2007 Grafton et al.
2007/0288031 A1 12/2007 Dreyfuss et al.
2007/0293879 A1 12/2007 Baker et al.
2008/0004659 A1 1/2008 Burkhart et al.
2008/0009904 A1 1/2008 Bourque et al.
2008/0027446 A1 1/2008 Stone et al.
2008/0027457 A1 1/2008 Dienst et al.
2008/0033488 A1 2/2008 Catanese et al.
2008/0046009 A1 2/2008 Albertorio et al.
2008/0058816 A1 3/2008 Philippon et al.
2008/0065080 A1 3/2008 Assell et al.
2008/0065092 A1 3/2008 Assell et al.
2008/0065114 A1 3/2008 Stone et al.
2008/0071282 A1 3/2008 Assell et al.
2008/0082127 A1 4/2008 Stone et al.
2008/0082128 A1 4/2008 Stone
2008/0086138 A1 4/2008 Stone et al.
2008/0103528 A1 5/2008 Zirps et al.
2008/0109037 A1 5/2008 Steiner et al.
2008/0114364 A1 5/2008 Goldin et al.
2008/0114399 A1 5/2008 Bonutti
2008/0132932 A1 6/2008 Hoeppner et al.
2008/0132948 A1 6/2008 Surti et al.
2008/0140078 A1 6/2008 Nelson et al.
2008/0140092 A1 6/2008 Stone et al.
2008/0140093 A1 6/2008 Stone et al.
2008/0140116 A1 6/2008 Bonutti
2008/0140123 A1 6/2008 Ferree
2008/0147063 A1 6/2008 Cauldwell et al.
2008/0147064 A1 6/2008 Cauldwell et al.
2008/0147071 A1 6/2008 Serra et al.
2008/0147119 A1 6/2008 Cauldwell et al.
2008/0154275 A1 6/2008 Assell et al.
2008/0161814 A1 7/2008 McAllister et al.
2008/0167660 A1 7/2008 Moreau et al.
2008/0188854 A1 8/2008 Moser
2008/0188935 A1 8/2008 Saylor et al.
2008/0243163 A1 10/2008 Masseglia et al.
2008/0249481 A1 10/2008 Crainich et al.
2008/0255613 A1 10/2008 Kaiser et al.
2008/0262544 A1 10/2008 Burkhart
2008/0275431 A1 11/2008 Stone et al.
2008/0275453 A1 11/2008 Lafosse et al.
2008/0275469 A1 11/2008 Fanton et al.
2008/0294177 A1 11/2008 To et al.
2008/0306483 A1 12/2008 Iannarone
2008/0306510 A1 12/2008 Stchur
2008/0312689 A1* 12/2008 Denham .................. D04C 1/06 606/228
2008/0319478 A1 12/2008 Foerster et al.
2009/0012526 A1 1/2009 Fletcher
2009/0018554 A1 1/2009 Thorne et al.
2009/0018654 A1 1/2009 Schmieding et al.
2009/0018655 A1* 1/2009 Brunelle ................... A61F 2/08 623/13.11
2009/0024130 A1 1/2009 Lombardo
2009/0054928 A1 2/2009 Denham et al.
2009/0062854 A1 3/2009 Kaiser et al.
2009/0076514 A1 3/2009 Haines
2009/0082805 A1 3/2009 Kaiser et al.
2009/0082807 A1 3/2009 Miller et al.
2009/0099554 A1 4/2009 Forster et al.
2009/0099598 A1 4/2009 McDevitt et al.
2009/0105775 A1 4/2009 Mitchell et al.
2009/0112208 A1 4/2009 Borgia et al.
2009/0112214 A1 4/2009 Philippon et al.
2009/0112270 A1 4/2009 Lunn et al.
2009/0112770 A1 4/2009 Schmidt et al.
2009/0131940 A1 5/2009 Brunnett et al.
2009/0138015 A1 5/2009 Conner et al.
2009/0138042 A1 5/2009 Tha
2009/0143784 A1 6/2009 Petersen et al.
2009/0143819 A1 6/2009 D'Agostino
2009/0149858 A1 6/2009 Fanelli et al.
2009/0157081 A1 6/2009 Homan et al.
2009/0157124 A1 6/2009 Ferragamo et al.
2009/0160112 A1 6/2009 Ostrovsky
2009/0171359 A1 7/2009 Sterrett
2009/0192468 A1 7/2009 Stone
2009/0192545 A1 7/2009 Workman
2009/0194446 A1 8/2009 Miller et al.
2009/0198258 A1 8/2009 Workman
2009/0210047 A1 8/2009 Amplatz et al.
2009/0216238 A1 8/2009 Stark
2009/0216243 A1 8/2009 Re
2009/0221922 A1 9/2009 Lec et al.
2009/0222013 A1 9/2009 Graf et al.
2009/0222041 A1 9/2009 Foerster
2009/0234386 A1 9/2009 Dean et al.
2009/0234451 A1 9/2009 Manderson
2009/0240104 A1 9/2009 Ogdahl et al.
2009/0240335 A1* 9/2009 Arcenio ............. A61B 17/7094 623/17.11
2009/0248029 A1 10/2009 Paulos
2009/0248068 A1 10/2009 Lombardo et al.
2009/0265002 A1 10/2009 Re et al.
2009/0292321 A1 11/2009 Collette
2009/0299386 A1 12/2009 Meridew
2009/0306671 A1 12/2009 McCormack et al.
2009/0306711 A1 12/2009 Stone et al.
2009/0312763 A1 12/2009 McCormack et al.
2009/0312776 A1 12/2009 Kaiser et al.
2009/0312792 A1 12/2009 Fallin et al.
2009/0312793 A1 12/2009 Huxel et al.
2009/0312794 A1 12/2009 Nason et al.
2009/0318961 A1 12/2009 Stone et al.
2009/0326538 A1 12/2009 Sennett et al.
2010/0004683 A1 1/2010 Hoof et al.
2010/0023056 A1 1/2010 Johansson et al.
2010/0049196 A1 2/2010 Re
2010/0049202 A1 2/2010 Re
2010/0049203 A1 2/2010 Re
2010/0049213 A1 2/2010 Serina et al.
2010/0057045 A1 3/2010 Albritton, IV et al.
2010/0063542 A1 3/2010 van der Burg et al.
2010/0069925 A1 3/2010 Friedman et al.
2010/0076440 A1 3/2010 Pamichev et al.
2010/0082033 A1 4/2010 Germain

(56) References Cited

U.S. PATENT DOCUMENTS

2010/0087857 A1 4/2010 Stone et al.
2010/0094314 A1 4/2010 Hernlund et al.
2010/0094355 A1 4/2010 Trenhaile
2010/0094425 A1 4/2010 Bentley et al.
2010/0100127 A1 4/2010 Trenhaile
2010/0114162 A1 5/2010 Bojarski et al.
2010/0121332 A1 5/2010 Crainich et al.
2010/0121333 A1 5/2010 Crainich et al.
2010/0121348 A1 5/2010 van der Burg et al.
2010/0121349 A1 5/2010 Meier et al.
2010/0137679 A1* 6/2010 Lashinski .......... A61B 17/0401 600/37
2010/0145341 A1 6/2010 Ranck et al.
2010/0145384 A1 6/2010 Stone et al.
2010/0152739 A1 6/2010 Sidebotham et al.
2010/0160962 A1 6/2010 Dreyfuss et al.
2010/0185238 A1 7/2010 Cauldwell et al.
2010/0185283 A1 7/2010 Baird et al.
2010/0191241 A1 7/2010 McCormack et al.
2010/0191283 A1 7/2010 Foerster et al.
2010/0198258 A1 8/2010 Heaven et al.
2010/0211075 A1 8/2010 Stone
2010/0222812 A1 9/2010 Stone et al.
2010/0222881 A1 9/2010 Prewett et al.
2010/0234947 A1 9/2010 Ben Rubi et al.
2010/0241121 A1 9/2010 Logan et al.
2010/0249786 A1 9/2010 Schmieding et al.
2010/0251861 A1 10/2010 Sixto, Jr. et al.
2010/0262146 A1 10/2010 Tulkis
2010/0262184 A1 10/2010 Dreyfuss
2010/0268275 A1 10/2010 Stone et al.
2010/0286694 A1 11/2010 Rio et al.
2010/0292713 A1 11/2010 Cohn et al.
2010/0292731 A1 11/2010 Gittings et al.
2010/0292732 A1 11/2010 Hirotsuka et al.
2010/0292792 A1 11/2010 Stone et al.
2010/0298878 A1 11/2010 Leung et al.
2010/0298879 A1 11/2010 Leung et al.
2010/0305576 A1 12/2010 Ferguson et al.
2010/0305709 A1 12/2010 Metzger et al.
2010/0318122 A1 12/2010 Leung et al.
2011/0009902 A1 1/2011 Leung et al.
2011/0015634 A1 1/2011 Smith et al.
2011/0015674 A1 1/2011 Howard et al.
2011/0015675 A1 1/2011 Howard et al.
2011/0022083 A1 1/2011 DiMatteo et al.
2011/0022084 A1 1/2011 Sengun et al.
2011/0046625 A1 2/2011 Boileau et al.
2011/0046682 A1 2/2011 Stephan et al.
2011/0054526 A1 3/2011 Stone et al.
2011/0071545 A1 3/2011 Pamichev et al.
2011/0071549 A1 3/2011 Caborn et al.
2011/0087247 A1 4/2011 Fung et al.
2011/0087280 A1 4/2011 Albertorio
2011/0087284 A1 4/2011 Stone et al.
2011/0093010 A1 4/2011 Genova et al.
2011/0098727 A1* 4/2011 Kaiser ................ A61B 17/0401 606/228
2011/0098728 A1 4/2011 McDevitt et al.
2011/0106089 A1 5/2011 Brunnett et al.
2011/0106153 A1 5/2011 Stone et al.
2011/0125189 A1 5/2011 Stoll, Jr. et al.
2011/0152927 A1 6/2011 Deng et al.
2011/0152929 A1 6/2011 McDevitt et al.
2011/0160767 A1 6/2011 Stone et al.
2011/0160768 A1 6/2011 Stone et al.
2011/0184516 A1 7/2011 Baird et al.
2011/0208194 A1 8/2011 Steiner et al.
2011/0208239 A1 8/2011 Stone et al.
2011/0208240 A1 8/2011 Stone et al.
2011/0213416 A1 9/2011 Kaiser
2011/0213417 A1 9/2011 Foerster et al.
2011/0218538 A1 9/2011 Sherman et al.
2011/0218625 A1 9/2011 Berelsman et al.
2011/0224726 A1 9/2011 Lombardo et al.
2011/0224799 A1 9/2011 Stone
2011/0238113 A1 9/2011 Fanton et al.
2011/0264138 A1 10/2011 Avelar et al.
2011/0264140 A1 10/2011 Lizardi et al.
2011/0264141 A1* 10/2011 Denham ............ A61B 17/0401 606/232
2011/0270278 A1 11/2011 Overes et al.
2011/0270293 A1 11/2011 Malla et al.
2011/0270306 A1 11/2011 Denham et al.
2011/0276090 A1 11/2011 Berndt et al.
2011/0295279 A1 12/2011 Stone et al.
2011/0301621 A1 12/2011 Oren et al.
2011/0301622 A1 12/2011 Oren et al.
2011/0301708 A1 12/2011 Stone et al.
2011/0319896 A1 12/2011 Papenfuss et al.
2012/0004672 A1 1/2012 Giap et al.
2012/0041485 A1 2/2012 Kaiser et al.
2012/0041486 A1 2/2012 Stone et al.
2012/0046693 A1 2/2012 Denham et al.
2012/0053591 A1 3/2012 Haines et al.
2012/0053629 A1 3/2012 Reiser et al.
2012/0053630 A1 3/2012 Denham et al.
2012/0053641 A1 3/2012 Meridew
2012/0059417 A1 3/2012 Norton et al.
2012/0059418 A1 3/2012 Denham et al.
2012/0071976 A1 3/2012 May et al.
2012/0089193 A1 4/2012 Stone et al.
2012/0095470 A1 4/2012 Kaiser et al.
2012/0095556 A1 4/2012 Re et al.
2012/0109142 A1 5/2012 Dayan
2012/0109156 A1 5/2012 Overes et al.
2012/0109194 A1 5/2012 Miller et al.
2012/0116452 A1 5/2012 Stone et al.
2012/0123474 A1 5/2012 Zajac et al.
2012/0130424 A1 5/2012 Sengun et al.
2012/0136388 A1 5/2012 Odermatt et al.
2012/0143221 A1 6/2012 Weisel et al.
2012/0150203 A1 6/2012 Brady et al.
2012/0150223 A1 6/2012 Manos et al.
2012/0150297 A1 6/2012 Denham et al.
2012/0150301 A1 6/2012 Gamache et al.
2012/0160050 A1 6/2012 Nishio et al.
2012/0165866 A1 6/2012 Kaiser et al.
2012/0165867 A1 6/2012 Denham et al.
2012/0165938 A1 6/2012 Denham et al.
2012/0172986 A1 7/2012 Stone et al.
2012/0179254 A1 7/2012 Saliman
2012/0180291 A1 7/2012 Oren et al.
2012/0197271 A1 8/2012 Astorino et al.
2012/0203231 A1 8/2012 Long et al.
2012/0203288 A1 8/2012 Lange et al.
2012/0209325 A1 8/2012 Gagliano et al.
2012/0239085 A1 9/2012 Schlotterback et al.
2012/0239086 A1 9/2012 Reznik et al.
2012/0245585 A1 9/2012 Kaiser et al.
2012/0253355 A1 10/2012 Murray et al.
2012/0265205 A1 10/2012 Steiner et al.
2012/0290002 A1 11/2012 Astorino
2012/0290004 A1 11/2012 Lombardo et al.
2012/0290006 A1 11/2012 Collins et al.
2012/0296345 A1 11/2012 Wack et al.
2012/0296427 A1 11/2012 Conner et al.
2012/0303046 A1 11/2012 Stone et al.
2013/0006276 A1 1/2013 Lantz et al.
2013/0012962 A1 1/2013 Stone
2013/0018416 A1 1/2013 Lombardo et al.
2013/0023928 A1 1/2013 Dreyfuss
2013/0023929 A1 1/2013 Sullivan et al.
2013/0023930 A1 1/2013 Stone et al.
2013/0035698 A1 2/2013 Stone et al.
2013/0046341 A1 2/2013 Stone et al.
2013/0053897 A1 2/2013 Brown et al.
2013/0072989 A1 3/2013 Overes et al.
2013/0085568 A1 4/2013 Smith et al.
2013/0096611 A1 4/2013 Sullivan
2013/0096612 A1 4/2013 Zajac et al.
2013/0103083 A1 4/2013 Baird
2013/0103084 A1 4/2013 Pamichev et al.
2013/0110165 A1 5/2013 Burkhart et al.

(56) References Cited

U.S. PATENT DOCUMENTS

| | | | |
|---|---|---|---|
| 2013/0116730 | A1 | 5/2013 | Denham et al. |
| 2013/0131722 | A1 | 5/2013 | Marchand et al. |
| 2013/0138152 | A1 | 5/2013 | Stone et al. |
| 2013/0144334 | A1 | 6/2013 | Bouduban et al. |
| 2013/0144338 | A1 | 6/2013 | Stone et al. |
| 2013/0158596 | A1 | 6/2013 | Miller et al. |
| 2013/0158601 | A1 | 6/2013 | Stone et al. |
| 2013/0165972 | A1 | 6/2013 | Sullivan |
| 2013/0178898 | A1 | 7/2013 | Arnett et al. |
| 2013/0184748 | A1 | 7/2013 | Sojka et al. |
| 2013/0190818 | A1 | 7/2013 | Norton |
| 2013/0190819 | A1 | 7/2013 | Norton |
| 2013/0204298 | A1 | 8/2013 | Graul et al. |
| 2013/0237997 | A1 | 9/2013 | Arai et al. |
| 2013/0238025 | A1 | 9/2013 | Howard et al. |
| 2013/0245700 | A1 | 9/2013 | Choinski |
| 2013/0267998 | A1 | 10/2013 | Vijay et al. |
| 2013/0268000 | A1 | 10/2013 | Harner et al. |
| 2013/0296893 | A1 | 11/2013 | Dean et al. |
| 2013/0296931 | A1 | 11/2013 | Sengun |
| 2013/0296934 | A1 | 11/2013 | Sengun |
| 2013/0317544 | A1 | 11/2013 | Ferguson et al. |
| 2013/0325063 | A1 | 12/2013 | Norton et al. |
| 2013/0345749 | A1 | 12/2013 | Sullivan et al. |
| 2014/0039503 | A1 | 2/2014 | Pilgeram |
| 2014/0081322 | A1 | 3/2014 | Sengun et al. |
| 2014/0135835 | A1 | 5/2014 | Stone et al. |
| 2014/0163679 | A1 | 6/2014 | Re et al. |
| 2014/0188163 | A1 | 7/2014 | Sengun |
| 2014/0257382 | A1 | 9/2014 | McCartney |
| 2014/0277121 | A1 | 9/2014 | Pilgeram et al. |
| 2014/0316460 | A1 | 10/2014 | Graul et al. |
| 2014/0364906 | A1 | 12/2014 | Palese et al. |

FOREIGN PATENT DOCUMENTS

| | | | |
|---|---|---|---|
| DE | 8903079 | U1 | 5/1989 |
| DE | 4231101 | A1 | 3/1994 |
| DE | 4243715 | A1 | 7/1994 |
| DE | 19503504 | A1 | 3/1996 |
| EP | 153831 | A2 | 9/1985 |
| EP | 0232049 | A1 | 8/1987 |
| EP | 0241240 | A2 | 10/1987 |
| EP | 251583 | | 1/1988 |
| EP | 253526 | A1 | 1/1988 |
| EP | 0270704 | A1 | 6/1988 |
| EP | 0318426 | B1 | 2/1991 |
| EP | 0440371 | A1 | 8/1991 |
| EP | 0574707 | A1 | 12/1993 |
| EP | 0611551 | A1 | 8/1994 |
| EP | 0673624 | A2 | 9/1995 |
| EP | 1016377 | A3 | 3/2001 |
| EP | 1155776 | A2 | 11/2001 |
| EP | 1174584 | A2 | 1/2002 |
| EP | 0834281 | B1 | 3/2003 |
| EP | 1369089 | A2 | 12/2003 |
| EP | 1398455 | A2 | 3/2004 |
| EP | 1825817 | A1 | 8/2007 |
| EP | 1568327 | B1 | 11/2009 |
| EP | 2277457 | A1 | 1/2011 |
| EP | 2286742 | A1 | 2/2011 |
| EP | 2335603 | | 6/2011 |
| EP | 2544607 | A1 | 1/2013 |
| EP | 2548519 | A2 | 1/2013 |
| EP | 2596755 | A2 | 5/2013 |
| EP | 2662030 | A1 | 11/2013 |
| EP | 2662032 | A1 | 11/2013 |
| EP | 1762187 | B1 | 10/2014 |
| FR | 1166884 | A | 11/1958 |
| FR | 2606996 | A1 | 5/1988 |
| FR | 2676638 | A1 | 11/1992 |
| GB | 2093353 | A | 9/1982 |
| WO | 9204874 | A1 | 4/1992 |
| WO | 95011631 | A1 | 5/1995 |
| WO | 9515726 | A1 | 6/1995 |
| WO | 9628100 | A1 | 9/1996 |
| WO | 9703615 | | 2/1997 |
| WO | 9704908 | A1 | 2/1997 |
| WO | 9722301 | A1 | 6/1997 |
| WO | 9730649 | A1 | 8/1997 |
| WO | 98038938 | A1 | 9/1998 |
| WO | 0024327 | A2 | 5/2000 |
| WO | 0044291 | A1 | 8/2000 |
| WO | 0128457 | A1 | 4/2001 |
| WO | 0160268 | A1 | 8/2001 |
| WO | 03007861 | A1 | 1/2003 |
| WO | 03086221 | A1 | 10/2003 |
| WO | 03092514 | A1 | 11/2003 |
| WO | 2004092531 | A2 | 10/2004 |
| WO | 2007/010389 | A1 | 1/2007 |
| WO | 2008063915 | A2 | 5/2008 |
| WO | 2008128075 | A1 | 10/2008 |
| WO | 2009105880 | A1 | 9/2009 |
| WO | 11060022 | A2 | 5/2011 |
| WO | 2011112371 | A1 | 9/2011 |
| WO | 2012034131 | | 3/2012 |
| WO | 2012134999 | A1 | 10/2012 |
| WO | 2012158583 | A1 | 11/2012 |
| WO | 2013006820 | A1 | 1/2013 |
| WO | 2014107729 | A2 | 7/2014 |

OTHER PUBLICATIONS

BIOMET Sports Medicine: Micromax Flex Suture Anchor, (2008).

Boccaccini, et al., "Composite Surgical Sutures with Bioactive Glass Coating", J Biomed Mater Res Part B: Appl Biomater 67B, pp. 618-626, 2003.

Bretcanu, et al., "Bioactivity of degradable polymer sutures coated with bioactive glass", Journal of Materials Science: Materials in Medicine, vol. 15, 2004, pp. 893-899.

Burkinshaw, U.S. Appl. No. 60/418,545, filed Oct. 15, 2002.

Canadian Office Action for Application No. 2,811,838 dated May 22, 2014.

Canadian Office Action for Application No. 2,812,775 dated Aug. 23, 2013.

Canadian Office Action for Application No. 2768020 dated Jan. 21, 2014.

Canadian Office Action for Application No. 2773849 dated Aug. 5, 2013.

Canadian Office Action for Application No. 2811838 dated Feb. 24, 2015.

Charles McCartney, U.S. Appl. No. 13/792,982, filed Mar. 11, 2013, titled "Filamentary Fixation Device and Assembly and Method of Assembly, Manufacture and Use".

Chen et al., European Cells and Materials, vol. 16, Supp. 4, p. 7, 2008.

Chen et al., Journal of Orthopaedic Research, pp. 1432-1438, Nov. 2009.

Chen et al., Poster No. 538, 54th Annual Meeting of the Orthopaedic Research Society, San Francisco, CA Mar. 2008.

Cole et al., American Journal of Sports Medicine, vol. XX, No. X, Apr. 2011, 10 pages.

Conmed: Linvatec: Shoulder Restoration System Y-Knot 1.3mm All Suture Anchor, Copyright 2011 Linvatec Corporation, a subsidiary of ConMed Corporation—CBR 3057 (4 pages).

European Search Report for Application No. 13178933.1 dated Sep. 25, 15.

European Search Report, EP 10173568, dated Nov. 30, 2010.

Extended European Search Report for Application No. EP 12164104 dated Jul. 11. 2012.

Extended European Search Report for Application No. EP14157129 dated Oct. 9, 2014.

Extended European Search Report for Application No. EP14157877 dated Jul. 4, 2016.

Extended European Search Report for Application No. EP14159656 dated Jun. 6, 2014.

HHS Tube, Fort Wayne Metals Research Products Corp., 2009, 2 pages.

(56) References Cited

OTHER PUBLICATIONS

Insall et al., The Journal of Bone and Joint Surgery, vol. 49B, No. 2, pp. 211-228, May 1967.
International Search Report and Written Opinion for Application No. PCT/US2012/024303 dated May 24, 2012.
International Search Report and Written Opinion for Application No. PCT/US2014/021231 dated Jun. 25, 2014.
International Search Report and Written Opinion for Application No. PCT/US2014/069087 dated Jun. 17, 2015.
International Search Report PCT/US2010/042264, dated Sep. 30, 2010.
Long et al., U.S. Appl. No. 13/368,730, filed Feb. 8, 2012, titled "Flexible Microdrilling Instrumentation, Kits and Methods".
Marchand et al., U.S. Appl. No. 13/303,849, filed Nov. 23, 2011, titled "Filamentary Suture Anchor".
Medtronic, The VISAO High-Speed Otologic Drill Catalog, 2007, 12 pages.
Partial European Search Report for U.S. Appl. No. 13/162,591 dated Aug. 14, 2015.
Partial European Search Report for Application No. EP14151822 dated May 16, 2014.
Partial European Search Report for Appln No. EP12193507 dated Jun. 30, 2017.
Partial International Search Report for Application No. PCT/US2014/069087 dated Mar. 12, 2015.
Perthes, German Surgery Periodical, vol. 85, Commermorative Publication, pp. 2-18, 1906.
Perthes, Uber Operationen bel habitueller Schulterluxaton, Deutsch Zeitschrift fur Chirurgie, vol. 85, 1906, pp. 199-227 (English translation provided.).
Pilgeram, Kyle Craig, U.S. Appl. No. 13/588,586, filed Aug. 17, 2012, titled "Soft Tissue Fixation Devices and Methods".
Pilgeram, Kyle Craig, U.S. Appl. No. 13/588,592, filed Aug. 17, 2012, titled "Surgical Instruments and Methods of Use".
Pilgeram, Kyle Craig, U.S. Appl. No. 13/783,804, filed Mar. 4, 2013, titled "Knotless Filamentary Fixation Devices, Assemblies and Systems and Methods of Assembly and Use".
Pilgeram, Kyle Craig, U.S. Appl. No. 61/679,336, filed Aug. 3, 2012, titled "Soft Tissue Fixation Device and Methods".
Stamboulis, et al., "Mechanical properties of biodegradable polymer sutures coated with bioactive glass", Journal of Materials Science: Materials in Medicine, vol. 13, 2002, pp. 843-848.
Steiner et al., U.S. Appl. No. 13/085,882, filed Apr. 13, 2011, titled "Flexible ACL Instrumentation, Kit and Method".
Sugaya et al., Journal of Bone and Joint Surgery, vol. 85-A, No. 5, pp. 878-884, May 2003.
U.S. Appl. No. 12/682,324, filed Sep. 7, 2010.
U.S. Appl. No. 13/070,692, filed Mar. 24, 2011.
U.S. Appl. No. 13/182,851, filed Jul. 14, 2011.
U.S. Appl. No. 13/799,773, filed Mar. 13, 2013.
European Examination Report for Application No. EP14157129.9 dated Jul. 28, 2017.
International Search Report for PCT/US2014/035018 dated Sep. 30, 2014.

* cited by examiner

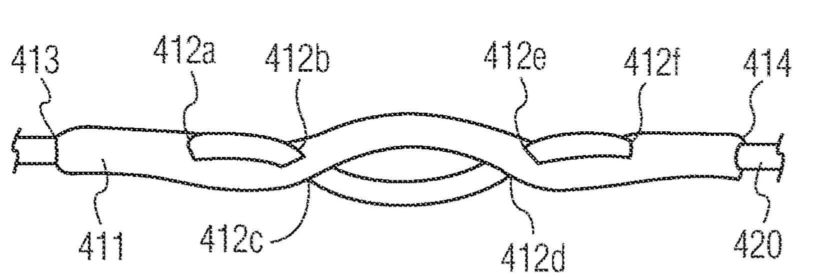
FIG. 10A
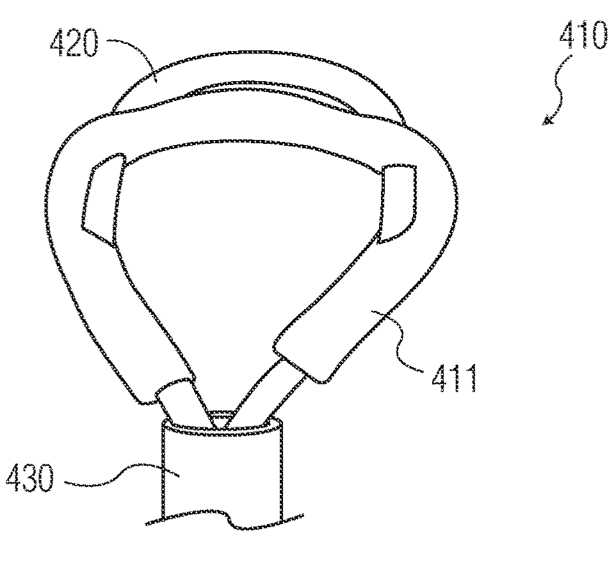
FIG. 10B
420
411
410
430
FIG. 10C

FILAMENTARY FIXATION DEVICE

CROSS REFERENCE TO RELATED APPLICATIONS

This application is a continuation of U.S. application Ser. No. 16/593,378, filed on Oct. 4, 2019, now U.S. Pat. No. 11,844,508, which is a continuation of U.S. application Ser. No. 15/243,183, filed on Aug. 22, 2016, now U.S. Pat. No. 10,448,944, which is a continuation of U.S. application Ser. No. 13/303,849, filed on Nov. 23, 2011, now U.S. Pat. No. 9,445,803, the disclosures of which are each incorporated herein by reference.

BACKGROUND OF THE INVENTION

Traditional fixation devices, such as suture anchors or tissue anchors, are typically made of metal or hard plastic, and include a structure which connects or otherwise secures a filament, such as a suture, or a portion of tissue, to the body of the device. In certain applications, these devices have a diameter suitable to hold the devices within a bone. Such devices may also include additional structures to dig into the bone, such as wings, barbs, threads, or the like.

However, such traditional devices tend to be large in diameter, and must include sufficient material, or other additional structures, to withstand the forces pulling against the device, whether via a suture or directly against the device itself. The size of such devices may limit the possible implantation locations in the body, as sufficient bone mass is required to accommodate the device. Moreover, a large hole must be drilled into the bone to allow for passage of the device through the cortical layer and into the cancellous bone. The larger drill holes may be too invasive resulting in excessive loss of healthy bone, or creation of a large repair site, resulting in prolonged recovery time and higher incidence of infection and other complications.

A recent trend in fixation device technology is the “soft” device, also referred to as an “all-suture” fixation device, in which the device itself is constructed of suture-like material. Such all-suture fixation devices may provide solutions to the various problems encountered with traditional devices, as summarized above.

BRIEF SUMMARY OF THE INVENTION

The present invention concerns, generally, a soft fixation device constructed substantially of filamentary material, such as suture or other thread-like material, which is capable of providing high pull-out strength while requiring a small surgical site (e.g., bone hole) as compared to traditional fixation devices. The present invention also includes various embodiments of such soft fixation devices, methods of insertion and related instrumentation, systems and kits. While the majority of embodiments disclosed herein relate to the use of the fixation device of the present invention as a suture anchor for placement in bone, other uses of the fixation device are also possible, many of which are also described herein.

In one embodiment, the present invention includes a fixation device including a sleeve member including an interior and an exterior surface along a length defined between a first end and a second end, and at least two openings positioned along the length and extending from the interior and through the exterior surface; and a filament including a first end and a second end and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member. The sleeve member may also be substantially hollow. The filament may further be adapted to be slidable through the interior of the sleeve.

Additionally, the exterior surface of the sleeve member may have at least four openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, and exit the interior through the second end of the sleeve member. Moreover, the exterior surface of the sleeve member may have at least six openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, exit the sleeve member through a fifth opening on the exterior surface, re-enter the sleeve member through a sixth opening on the exterior surface and into the interior, and exit the interior through the second end of the sleeve member.

The sleeve may further be pliable and also expandable or compressible. The filament may also be adapted to be slidable through the sleeve member when the sleeve member is expanded or compressed. The filament may not overlap itself within the interior of the sleeve member. The filament may pass through the interior of the sleeve member in a single direction along the length of the sleeve member.

Moreover, at least one of the filament and the interior may include a coating adapted to improve sliding of the filament through the interior. The exterior surface of the sleeve may also include a coating which may be adapted to allow for tissue ingrowth. The filament may also include a coating adapted to promote healing in adjacent tissue. The filament may also include an at least one indicating marker along its length. Further, the filament may also include multiple colors or patterns along its length, wherein the filament may include one color along a portion of the filament and a second color along another portion of the filament, wherein the colors may provide a distinguishing feature between the two portions of the filament.

In another embodiment, the present invention may include a sleeve member including an interior and an exterior surface along a length defined between a first end and a second end, and at least two openings positioned along the length and extending from the interior and through the exterior surface; and a filament including a first free end and a second free end and a length therebetween, the filament positioned relative to the sleeve member such that the free ends extend from the sleeve member at the first and second ends of the sleeve member, the filament being disposed inside the interior from the first end to a first opening, outside the sleeve member from the first opening to a second opening, and inside the interior from the second opening to the second end of the sleeve member. The sleeve member may further be substantially hollow.

Moreover, the exterior surface of the sleeve member may have at least four openings positioned along its length, such that the filament may be disposed inside the interior from the first end to a first opening, outside the sleeve member from the first opening to a second opening, inside the interior from the second opening to a third opening, outside the sleeve member from the third opening to a fourth opening, and inside the interior from the fourth opening to the second end of the sleeve member. Alternatively, the exterior surface of the sleeve member may have at least six openings positioned along its length, such that the filament may be disposed inside the interior from the first end to a first opening, outside the sleeve member from the first opening to a second opening, inside the interior from the second opening to a third opening, outside the sleeve member from the third opening to a fourth opening, inside the interior from the fourth opening to a fifth opening, outside the sleeve member from the fifth opening to a sixth opening, and inside the interior from the sixth opening to the second end of the sleeve member.

The filament may further be adapted to be slidable through the interior of the sleeve member. At least one of the filament and sleeve member may also include a coating. For example, at least one of the filament and the interior may include a coating adapted to improve sliding of the filament through the interior. In addition to, or alternatively, the exterior surface of the sleeve may include a coating adapted to allow for tissue ingrowth. Further, the filament may include a coating adapted to promote healing in adjacent tissue.

Moreover, the sleeve member may be pliable and may be expandable or compressible, wherein the filament may be adapted to be slidable through the sleeve member when the sleeve member is expanded or compressed.

Also, the filament may pass through the interior of the sleeve member in a single direction along the length of the sleeve member. The filament may further include an at least one indicating marker along its length. The filament may further include one color along a portion of the filament and a second color along another portion of the filament, wherein the colors provide a distinguishing feature between the two portions of the filament.

In yet another embodiment, the present invention may include a fixation device including a sleeve member including a length, an interior and an exterior surface defined along the length, and at least two openings positioned along the length through the exterior surface; and a filament comprising a first end and a second end and a length therebetween, the filament positioned relative to the sleeve member such that the filament exits the sleeve member through one of the openings on the exterior surface of the sleeve and re-enters the sleeve member through the other opening on the exterior surface and into the interior such that the filament passes through the interior of the sleeve member in a single direction and is adapted to be slidable through the interior of the sleeve member along the length of the filament. The sleeve member may also be substantially hollow and may further include a first end and a second end at respective ends of the length, and the filament may thus enter the interior of the sleeve member through the first end and exit through the second end.

Additionally, the exterior surface of the sleeve member may have at least four openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, and exit the interior through the second end of the sleeve member. Moreover, the exterior surface of the sleeve member may have at least six openings positioned along its length, such that the filament may enter the interior through the first end, exit the sleeve member through one of the openings on the exterior surface, re-enter the sleeve member through a second opening on the exterior surface and into the interior, exit the sleeve member through a third opening on the exterior surface, re-enter the sleeve member through a fourth opening on the exterior surface and into the interior, exit the sleeve member through a fifth opening on the exterior surface, re-enter the sleeve member through a sixth opening on the exterior surface and into the interior, and exit the interior through the second end of the sleeve member.

In a further embodiment, the present invention may include a fixation device including a sleeve member including an interior and an exterior surface along a length defined between a first end and a second end, and at least two openings positioned along the length and extending from the interior and through the exterior surface; and a filament including a first end and a second end, a length therebetween, and an at least one indicating marker positioned along its length, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member. The sleeve member may also be substantially hollow. The filament may further be adapted to be slidable through the interior of the sleeve. The indicating marker may be adapted to provide guidance to an operator that proper deployment of the device has occurred.

In yet a further embodiment, the present invention may include a fixation device including a sleeve member including an interior and an exterior surface along a length defined between a first end and a second end, and at least two openings positioned along the length and extending from the interior and through the exterior surface; and a filament including a first end and a second end and a length therebetween, the filament positioned relative to the sleeve member such that the filament enters through the first end into the interior, sequentially exits and re-enters the sleeve member through consecutive openings on the exterior surface of the sleeve, and exits the interior through the second end of the sleeve member such that the filament is disposed outside of the sleeve member in X regions along the length of the sleeve member, is disposed inside the interior in X+1 regions along the length or the sleeve member, and passes through openings numbering 2X, wherein X≥1. The sleeve member may also be substantially hollow. The filament may further be adapted to be slidable through the interior of the sleeve.

In another embodiment, the present invention may include a system including a fixation device including a sleeve member including an interior and an exterior surface along a length defined between a first end and a second end, and at least two openings positioned along the length and extending from the interior and through the exterior surface; and a filament including a first end and a second end, and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member; and an inserter. The inserter may include a distal tip which engages a portion of the fixation device. Further, the distal tip may engage, directly, both a portion of the sleeve and a portion of the filament which has exited the sleeve member through one of the openings.

In yet another embodiment, the present invention may include a method for securing a filament in a hole in a bone, including: accessing the bone and preparing a bone hole; inserting a fixation device into the bone hole, the device including a sleeve member including an interior and an exterior surface along a length defined between a first end and a second end, and at least two openings positioned along the length through the exterior surface; and a filament including a first end and a second end and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member; and compressing the sleeve member within the bone hole. As to the compressing step, the two ends of the filament may be pulled. Alternatively, the compressing step may include sequentially pulling on one end of the filament and pulling on the other end of the filament. This method may further include the step of adjusting the filament by pulling on at least one of the two ends of the filament to slide the filament through the sleeve member. Further, the step of compressing the sleeve member may change the shape of the sleeve member from a substantially U-shape to a substantially W-shape. In a further step, this method may include using the filament secured in bone to thereby secure tissue to the bone, including the steps of passing at least one end of the filament through the tissue and securing the tissue to the bone by securing the filament thereto. The filament may be secured to the tissue, to thereby secure the tissue to bone, through a knot or the like.

In a further embodiment, the present invention may include a method for securing a tissue to a bone, including: accessing the bone and preparing a bone hole; inserting a fixation device into the bone hole, the device including a sleeve member having an interior and an exterior surface along a length defined between a first end and a second end, and at least two openings positioned along the length through the exterior surface; and a filament including a first end and a second end and a length therebetween, the filament positioned relative to the sleeve member such that the filament enters through the first end and into the interior, exits the sleeve member through one of the openings on the exterior surface of the sleeve, re-enters the sleeve member through the other opening on the exterior surface and into the interior, and exits the interior through the second end of the sleeve member; pulling on the two ends of the filament to compress the sleeve member within the bone hole; adjusting the filament by pulling on at least one of the two ends of the filament; passing at least one end of the filament through the tissue; and securing the tissue to the bone by securing the filament thereto. The tissue may be a portion of a rotator cuff, a portion of a shoulder labrum, a portion of a hip labrum, or another soft tissue, any of which may be reattached to the bone at a reattachment site at or adjacent to the bone hole. This device can also be deployed into soft tissue to secure soft tissue to soft tissue such as meniscal repair or the like. Furthermore, this device can also be deployed into bone to secure bone to bone such as fracture fixation or the like.

BRIEF DESCRIPTION OF THE DRAWINGS

FIGS. 10A-C illustrate another embodiment of a fixation device of the present invention.

DETAILED DESCRIPTION

The fixation device, and associated systems, kits and methods, of the present invention are intended for use in tissue, such as bone or soft tissue. Soft tissue may be, for example, meniscus, cartilage, ligaments and tendons, or the like. While many of the exemplary methods disclosed herein are directed towards its use as a suture anchor for implantation into a bone hole, other uses, some of which are described herein, are also envisioned. As used herein, "proximal" or "proximally" means closer to or towards an operator, e.g., surgeon, while "distal" or "distally" means further from or away from the operator.

Figure 1:
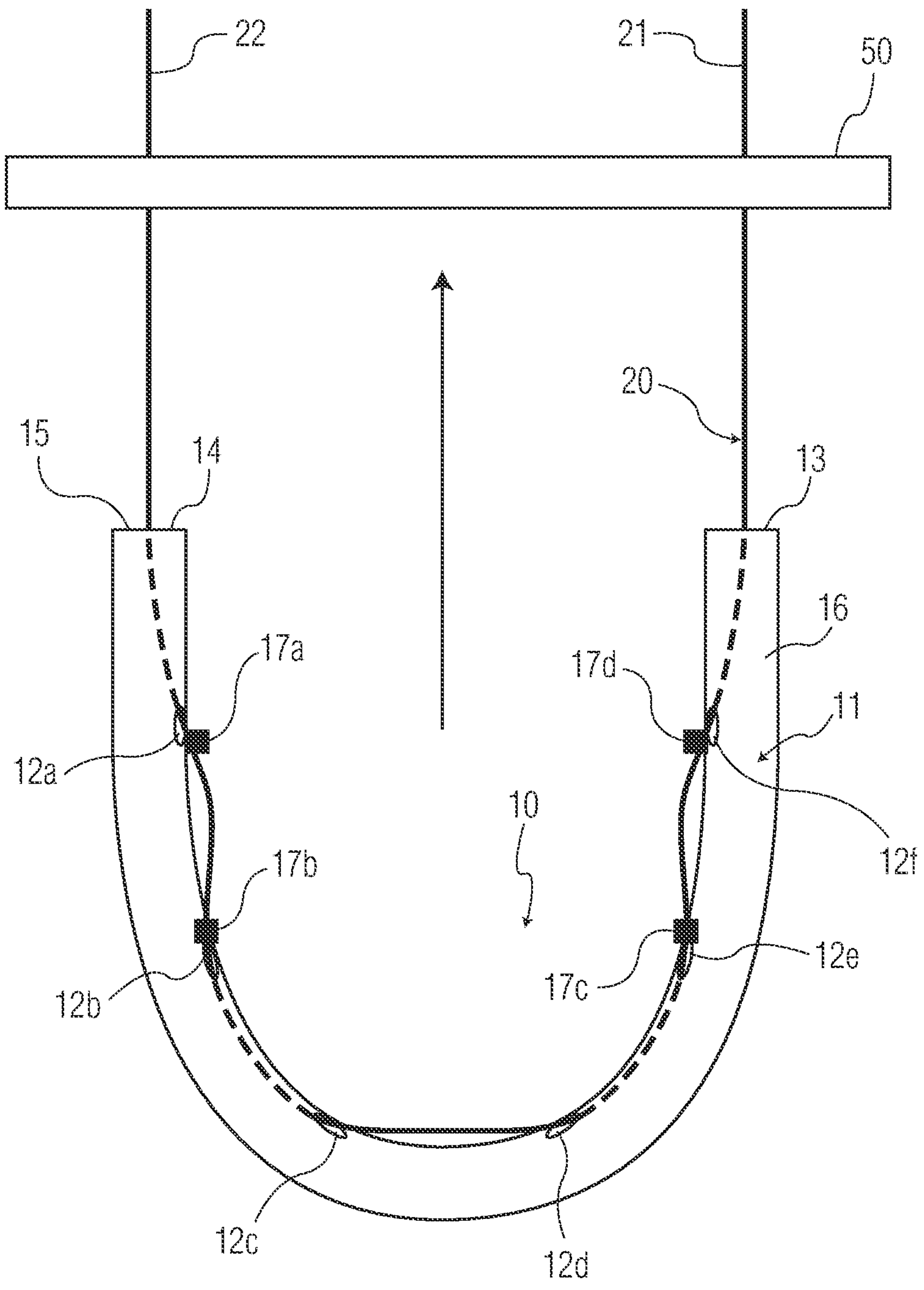
FIG. 1 illustrates one embodiment of a fixation device of the present invention.
Figure 2:
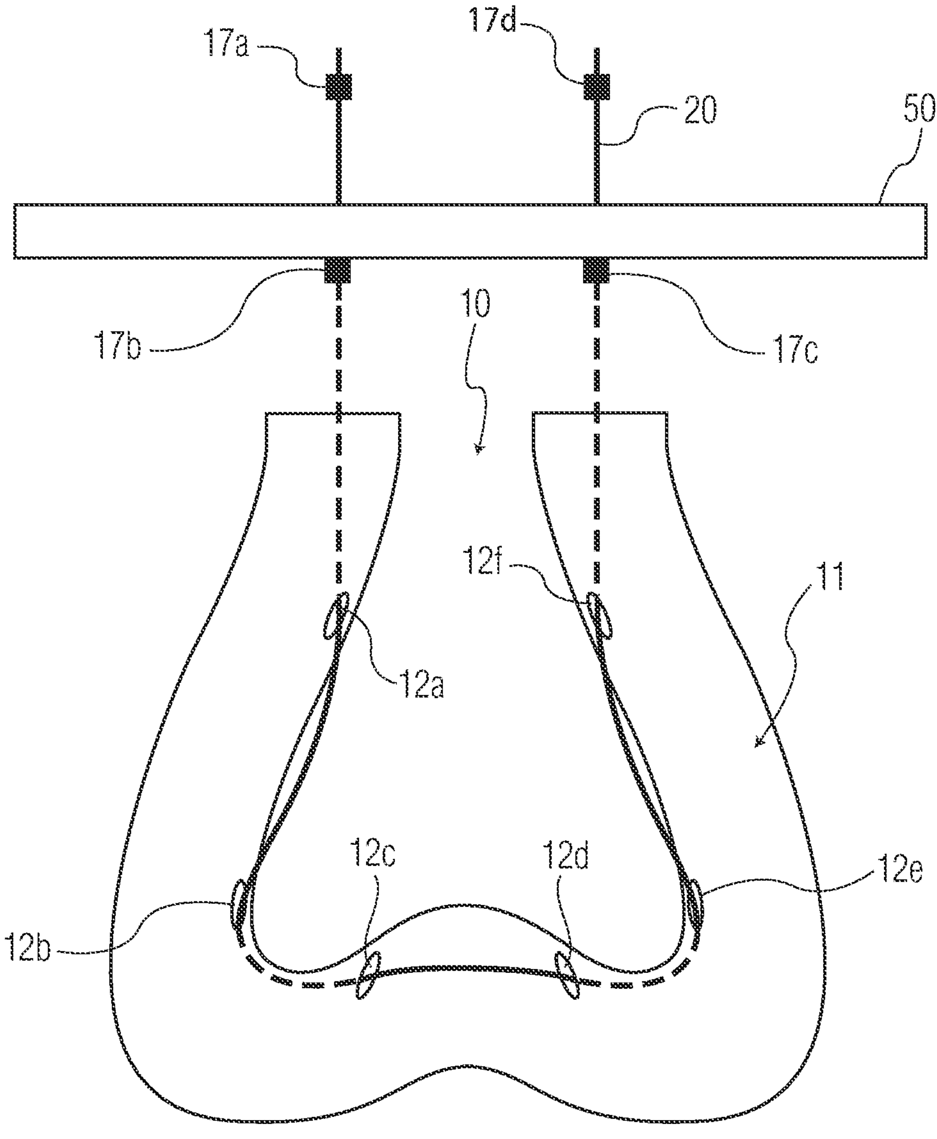
FIG. 2 illustrates the fixation device of FIG. 1 after tensioning of the filament 20.

In a first embodiment, illustrated in FIGS. 1 and 2, the fixation device 10 of the present invention includes a sleeve member 11 and a filament 20. The sleeve member 11 includes an interior 15 and an exterior surface 16, both of which extend along a length defined between a first end 14 and a second end 13. The sleeve member 11 may be substantially hollow. The exterior surface also includes at least two openings 12*c*, 12*d* positioned along the length of the exterior surface 16, each of which form a passageway through the exterior surface and into the interior 15. As illustrated, though, the exterior surface may include more than two openings, and may include four openings (for example, 12*a*, 12*b*, 12*e*, 12*f*), six openings (for example, 12*a*, 12*b*, 12*c*, 12*d*, 12*e*, 12*f*), or any other number of openings in any configuration positioned along the length of the exterior surface. The various openings 12 may be prepared, for example, during the weaving process forming the sleeve 11 or, alternatively, the openings may be formed after the sleeve has been woven, such as by the use of a needle, knife, or other tool capable of forming the openings.

The filament 20 includes a length and at least a portion of the length of the filament is positioned within the interior 15 of sleeve 11. The filament also includes first and second free ends 21, 22. The filament is slidable within the interior 15. The filament may also pass through at least one of the openings 12 along the exterior surface 16 of the sleeve 11. For example, as in FIG. 1, filament 20 may exit the interior 15 through opening 12*c* and re-enter the interior through opening 12*d*.

In one embodiment, the fixation device 10 of the present invention may include a sleeve member 11 including an interior 15 and an exterior surface 16 along a length defined between a first end 14 and a second end 13, and at least two openings 12 positioned along the length and extending from the interior and through the exterior surface; and a filament 20 including a first free end 22 and a second free end 21 and a length therebetween, the filament positioned relative to the sleeve member such that the free ends extend from the sleeve member at the first and second ends of the sleeve member, the filament being disposed inside the interior from the first end 14 to a first opening 12*a*, outside the sleeve member from the first opening to a second opening 12*b*, and inside the interior from the second opening to the second end 13 of the sleeve member. The sleeve member may further be substantially hollow.

Figure 14A:
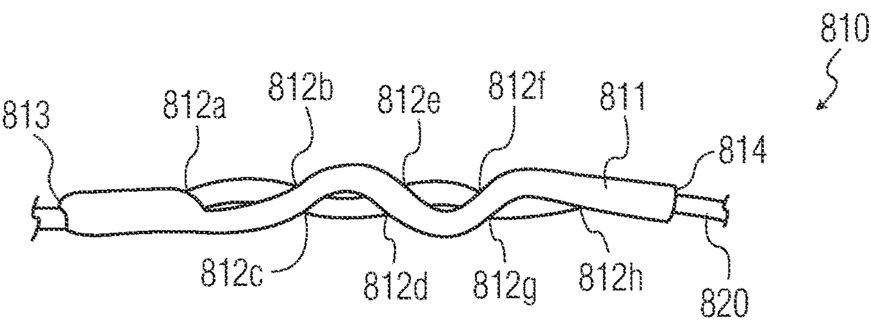
FIGS. 14A-C illustrate a further embodiment of a fixation device of the present invention.
Figure 14B:
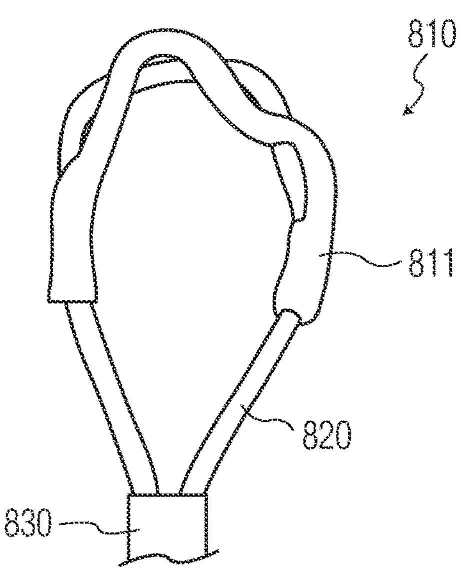
Figure 14C:
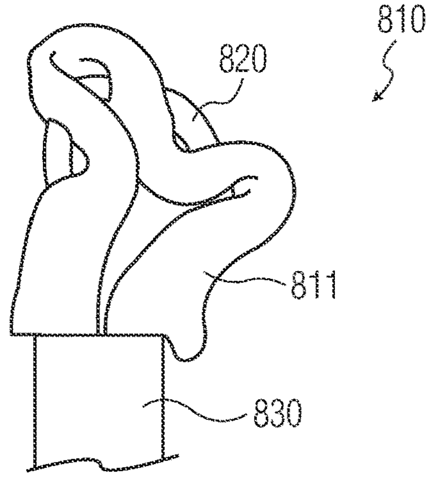
Figure 15A:
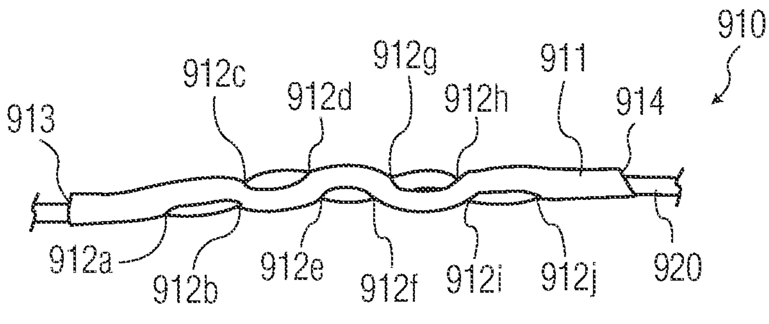
FIGS. 15A-C illustrate still another embodiment of a fixation device of the present invention.
Figure 15B:
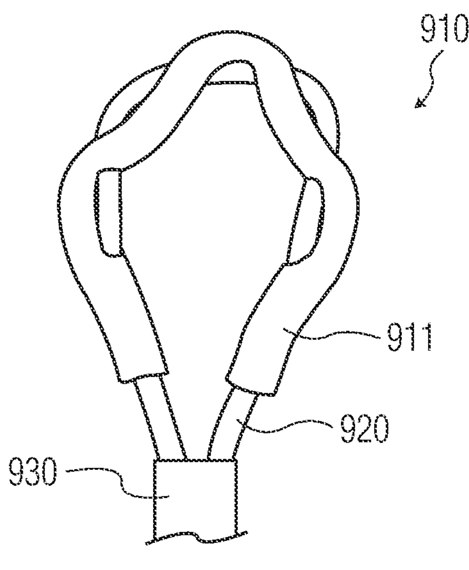
Figure 15C:
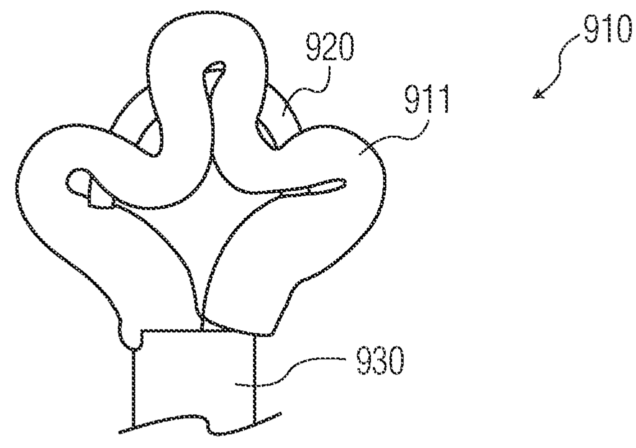
Figure 16A:
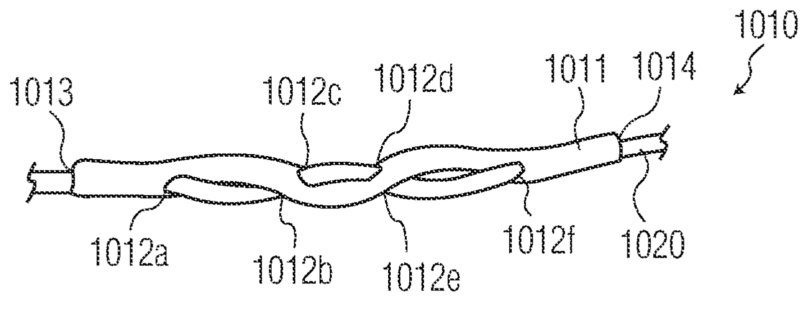
FIGS. 16A-C illustrate another embodiment of a fixation device of the present invention.
Figure 16B:
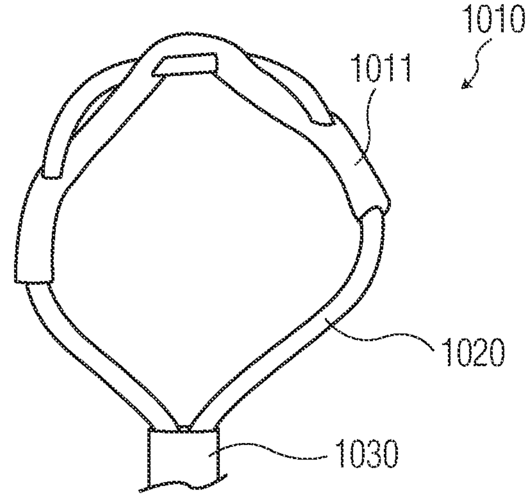
Figure 16C:
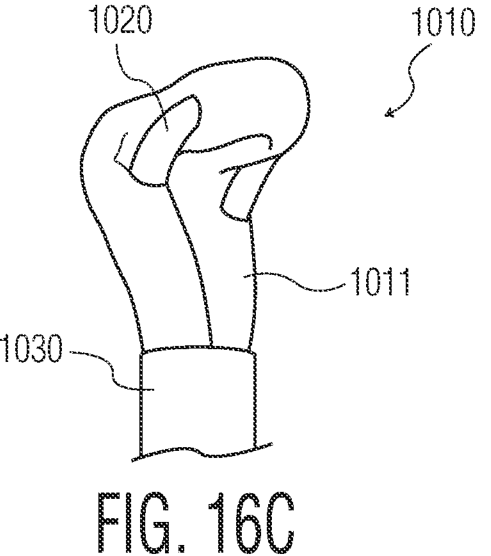

Put another way, in one embodiment, the present invention may include a fixation device including a sleeve member including an interior and an exterior surface along a length defined between a first end and a second end, and at least two openings positioned along the length and extending from the interior and through the exterior surface; and a filament including a first end and a second end and a length therebetween, the filament positioned relative to the sleeve member such that the filament enters through the first end into the interior, sequentially exits and re-enters the sleeve member through consecutive openings on the exterior surface of the sleeve, and exits the interior through the second end of the sleeve member such that the filament is disposed outside of the sleeve member in X regions along the length of the sleeve member, is disposed inside the interior in X+1 regions along the length or the sleeve member, and passes through openings numbering 2X, wherein X≥1. The various exemplary embodiments illustrated in this application show that, for example, X=2 (as in FIGS. 5-6, for example); X=3 (as in FIGS. 1-4, 7-13 and 16, for example); X=4 (as in FIGS. 14A-C, for example); X=5 (as in FIGS. 15A-C).

The filament 20 may be, for example, a length of suture or other such material. The filament may be substantially hollow or substantially solid, and may further have a substantially round or substantially flat (e.g., tape) shape. The filament may also include, for example, a relatively stiff portion, relative to the rest of the filament, which can provide beneficial uses such as for simpler threading through small devices, such as a fixation device like a ReelX suture anchor (Stryker Endoscopy, San Jose, CA), or to provide a stiff portion which may be pushed through a cannula or other instrument, such as a suture passer. The sleeve 11 may also be, for example, a suture or other such material that is substantially hollow forming the interior 15. The sleeve, like the filament, may also include a stiff portion or portions which may provide for better placement on an inserter, such as by helping the sleeve to fold around the end of the inserter. Both the sleeve and the filament may be constructed by known means, such as by braiding multiple filaments together, as is the normal manufacturing process of sutures and the like. Either or both of the filament and sleeve may be constructed of synthetic material (e.g., PLGA, UHMWPE, or the like) or of organic material (silk, animal tendon, or the like).

The filament 20 may also optionally include at least one indicating marker 17*a*, 17*b*, 17*c* and 17*d* which may indicate to an operator, such as a surgeon, whether or not the device 10 is properly positioned and/or compressed, as will be explained in greater detail below. The indicating marker may be, for example, a spot (as illustrated), a radial ring, a portion having a differing color from the rest of the filament, or the like. In another example, the indicating markers 17*a-d* of the filament 20 may be a portion of the filament 20 being of a different color than the rest of the filament. In this example, the portion of filament 20 between reference numbers 17*a* and 17*b*, and between 17*c* and 17*d*, may be of a different color than the remainder of the filament 20. Such contrasting colors of these portions may provide a clear indication to the operator when performing a surgical procedure, and may be of particular use in arthroscopic procedures.

Further, the filament 20 may also include a color or other pattern along its length. For example, the filament 20 may be of a certain color such that an operator may know which suture, among numerous others which may be present at the surgical site, is the filament 20. Moreover, filament 20 may have multiple colors or patterns along its length, other than those represented as the at least one indicating marker. For example, one half of the filament 20 may be one color, and the other half of the filament may be a different color. If the particular surgery requires that the two ends of filament 20 be tied together, such as by a slip knot, the two different colors may assist the operator in knowing which half of the filament should be used as the post and which half should be used to tie the slip knot around the post. Such a decision would be based on the particular surgical procedure being performed. Of course, the two differing colors may cover different amount of the length of the filament, however, the differing colors may be most useful if they cover at least the two free ends or end portions 21, 22 of the filament such that an operator can easily differentiate between the two lengths of the filament.

The sleeve has a diameter at least as large as the filament such that the sleeve has an inner diameter of sufficient size to allow the filament to pass therethrough and be slidable therein. Various arrangements of sizes of filament and sleeve are envisioned, so long as the filament remains slidable through the sleeve. For example, in one embodiment, the filament 20 may be a #2 suture while the device 10, positioned on an inserter, may have a diameter of about 1.2 mm. In one exemplary use of the device, where the device is positioned within a bore hole in tissue, such as bone, this sized device 10 may be positioned within a bore hole in tissue having a diameter of about 0.8-1.6 mm, preferably about 1.20-1.45 mm. In an alternative embodiment of the device 10, two filaments 20 may be included within a single sleeve 11, where the filaments are both #2 suture and the device 10, positioned on an inserter, may have a diameter of about 1.8-2.6 mm, and preferably about 1.9 mm. This sized device may also be positioned, for example, within a bore hole in tissue having a diameter of about 1.5-3.0 mm, preferably about 1.9-2.3 mm. This size of a bore hole may also be used for an alternative embodiment of the device 10 including three filaments 20 within a single sleeve 11. During use, the sleeve, being a length of filamentary material, may stretch or otherwise expand such that the effective diameter of the sleeve may be larger than the examples provided above. Of course, many other configurations of filament and sleeve sizes are envisioned depending on the surgical location and procedure.

Figure 3A:
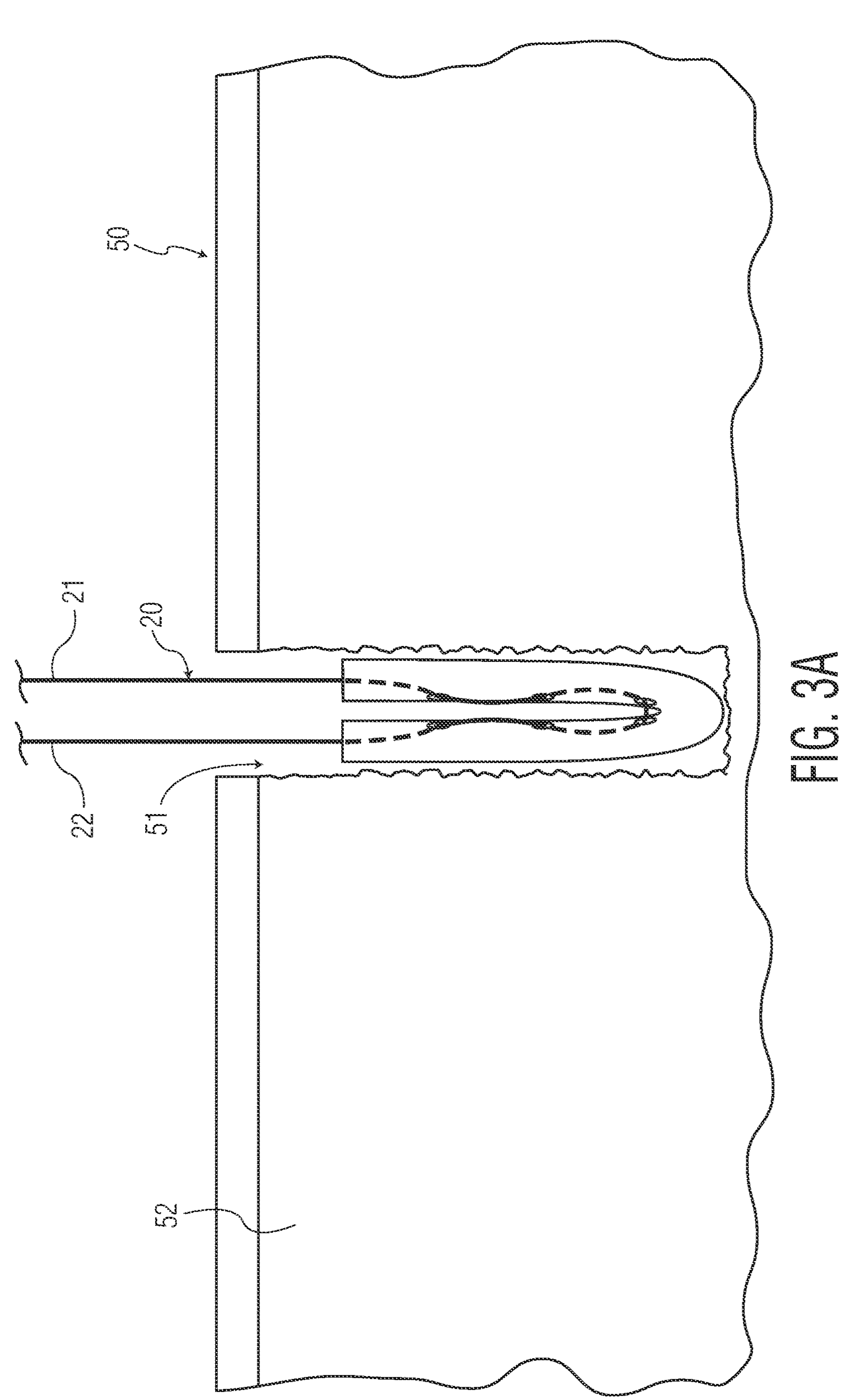
FIG. 3A illustrates one embodiment of a method of insertion of the fixation device of FIG. 1, wherein the fixation device is positioned within a hole prepared in a bone.
Figure 3B:
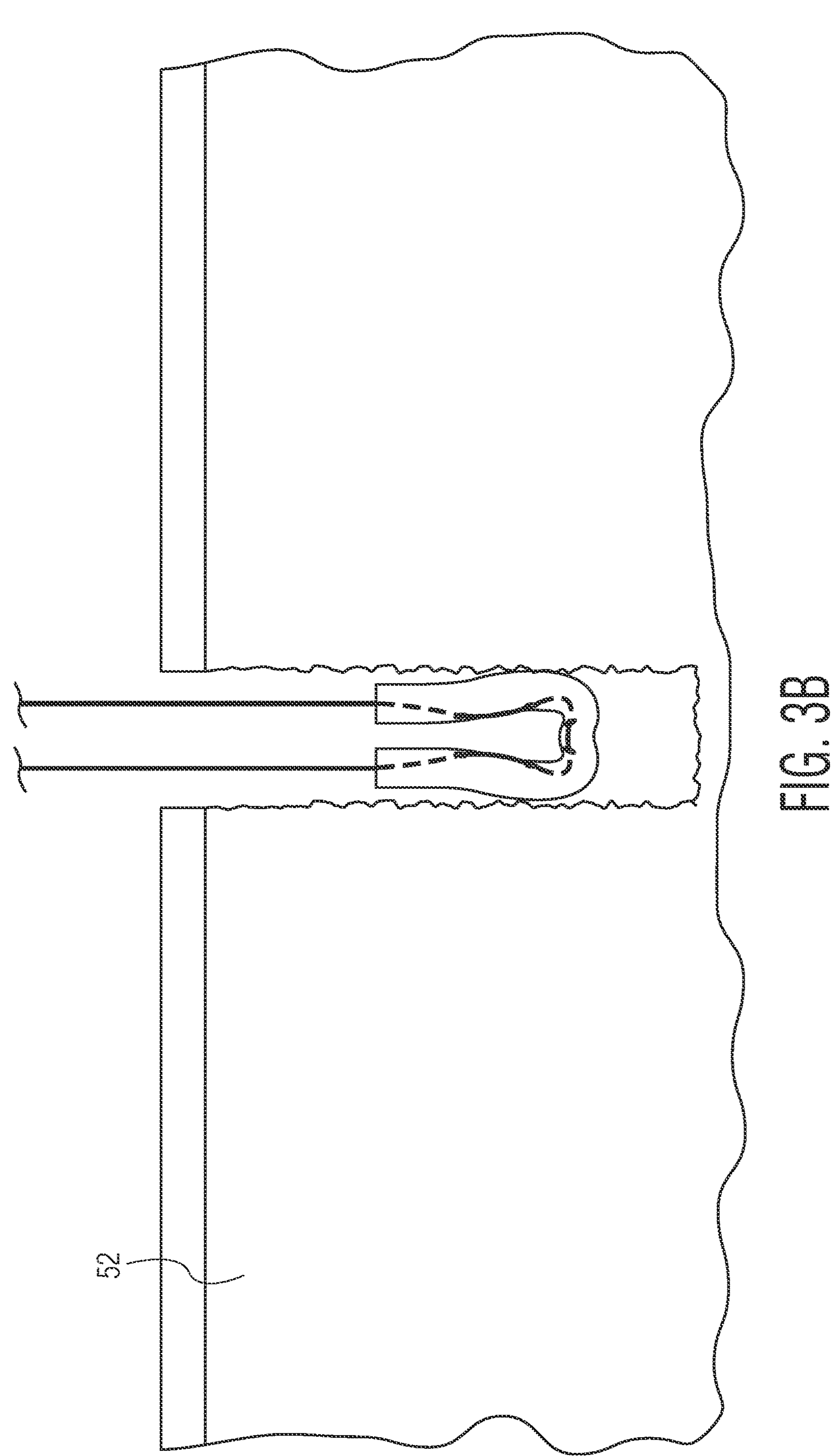
FIG. 3B illustrates the fixation device of FIGS. 1 and 2, in which the filament 20 is tensioned and the fixation device is compressed.
Figure 3C:
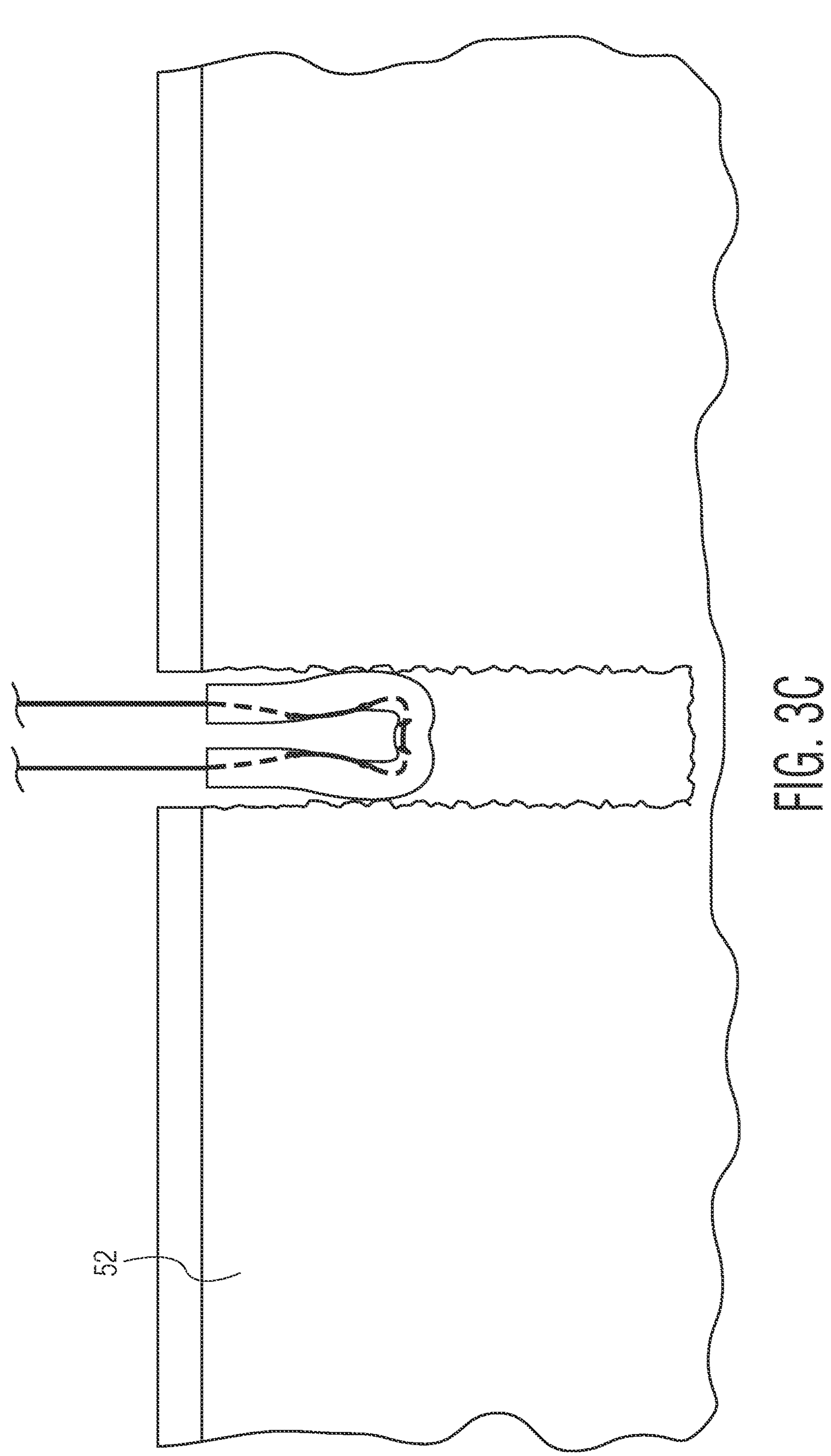
FIG. 3C illustrates potential migration of the fixation device proximally, towards the cortical bone.

Additionally, the sleeve is flexible and is further expandable and compressible which may allow the sleeve, upon tensioning of the filament to, for example, adjust from a substantially U-shape (e.g., FIGS. 1, 3A) and compact or crush, or otherwise compress, to a substantially W-shape (e.g., FIGS. 2, 3B-C). As the sleeve compresses, the diameter of the sleeve may increase and the height of the sleeve may decrease. This shape change during compression provides for increased pullout strength as the sleeve further engages the cancellous bone and/or cortical bone in this compressed shape, as seen for example in FIGS. 3B-C.

The pullout strength may also depend on the positioning of the openings 12 along the sleeve, and particularly, the positioning of the middle openings, which are positioned toward the base of the U-shape, prior to compression of the sleeve, and which, during compression, assist in forming the W-shape of the sleeve. For example, as to the embodiment of FIGS. 1-4, the openings 12*c* and 12*d* may be spaced apart at a distance such that at least 3 mm of filament spans the distance between the openings 12*c*, 12*d*, and more preferably, at least 6 mm of filament span the distance between the openings 12*c*, 12*d*. Such distance between openings 12*c*, 12*d* may allow for a larger amount of sleeve material to be present between the openings, such that as the sleeve is compressed, this larger amount of material creates a W-shape, as in FIG. 3B-C, which may affect an increased pullout strength of the device. If less than 3 mm of filament spans between openings 12*c*, 12*d*, there will also be less sleeve material between the openings, which may result in decreased pullout strength due to less material forming the middle of the compressed W-shape. Moreover, as discussed in greater detail below, the span of filament, outside of the sleeve, between openings 12*c* and 12*d* may allow for better seating on an insertion device 30 (FIG. 4) such that, for example, the device 10 may fit through a smaller bore hole in a tissue than if the filament were positioned within the sleeve between openings 12*c* and 12*d*.

Similarly, the openings near the ends of the sleeve, for example, openings 12*a*, 12*f* of FIG. 1, may be positioned at least 3 mm from the ends 13, 14 of the sleeve to maintain sleeve strength. If the openings 12*a*, 12*f* are placed too close to the ends, such as less than 3 mm away from the ends, the sleeve may break during compression, which may result in decreased pullout strength.

The fixation device is constructed, in one embodiment, by weaving two separate filament-like structures, the sleeve 11 and the filament 20, using known materials (such as sutures or the like) in a specific weaving process. In one example, a needle (not shown) may be used to pass the filament 20 (attached to the needle) through the interior 15 of the sleeve, from the first end 14 to the second end 13. The filament may be directed through the various openings 12 through the sleeve 11 and finally be pulled out through the second end 14. Following assembly, the fixation device 10 is now ready for packaging, sterilization, and subsequent use. In order to allow for proper sliding of the filament 20 through the sleeve 11, the filament may be passed through the interior of the sleeve such that the filament does not overlap itself, as can be seen in the various embodiments illustrated in the figures. As can also be seen in the various figures, in order to allow for the sliding of the filament 20, the filament is passed through the interior of the sleeve member in a single direction along the length of the sleeve member. Such configurations of the sleeve and filament may provide decreased friction between the sleeve and filament such that the filament has an increased ability to slide, even when the sleeve is compressed.

Sliding of the filament 20 within the sleeve 11 may be improved through the introduction of a coating on at least one of the interior 15 of the sleeve and the filament 20. Suitable coatings may include PTFE or the like which minimizes friction between the filament and the sleeve and improves sliding.

Other coatings may also be applied to at least one of the filament and sleeve. For example, the exterior surface 16 of the sleeve 11 may have a coating suitable for allowing tissue ingrowth. Such a suitable coating may be hydroxyapatite powder or tricalcium phosphate for promoting bone ingrowth. Other coatings may include collagen-based additives, platelet—rich plasma, bioactive glass, or the like, to be used depending on the type of tissue into which the device 10 is being placed.

Figure 4:
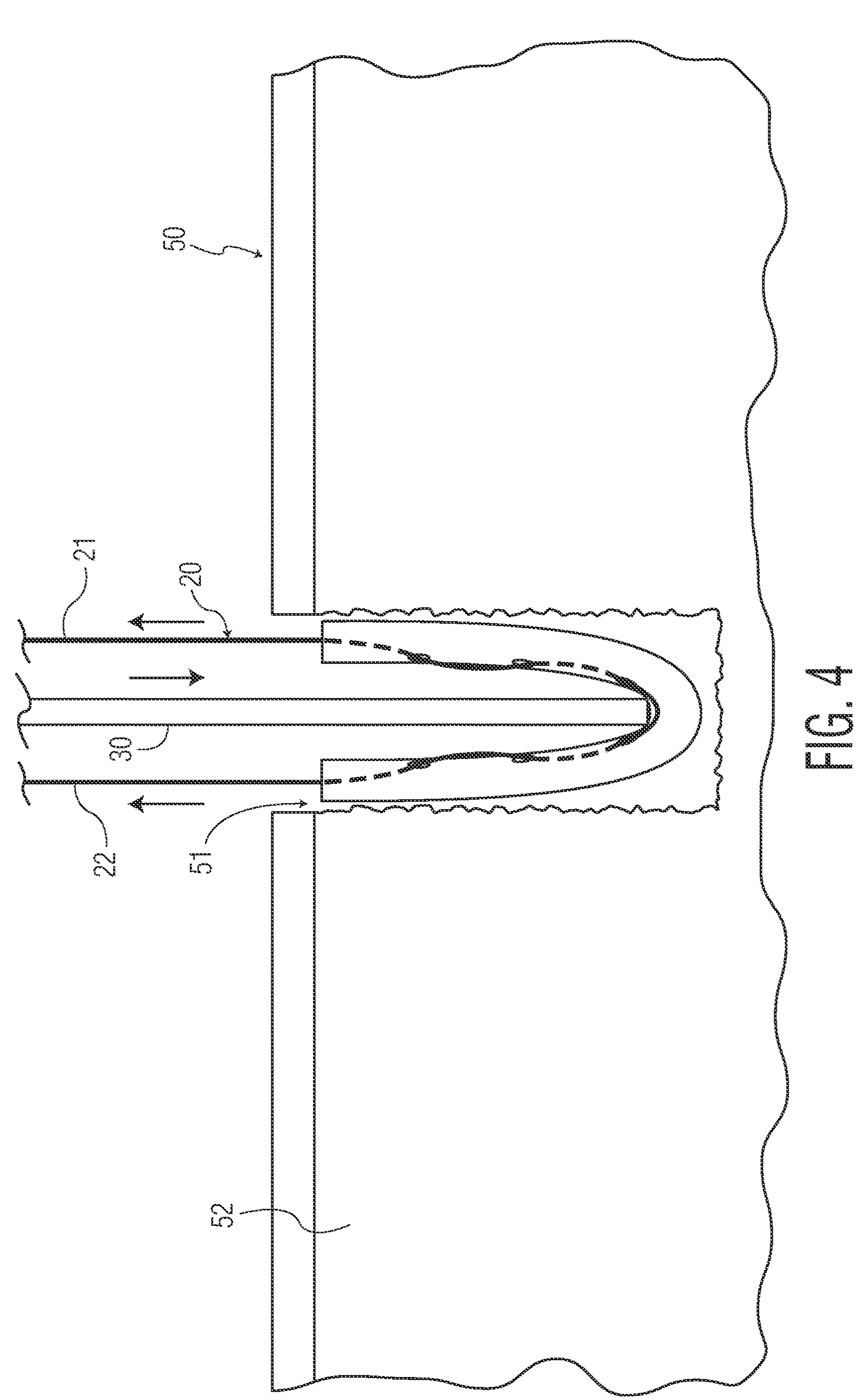
FIG. 4 illustrates one embodiment of a method of insertion of the fixation device of FIGS. 1 and 2, in which an insertion tool is used to implant the fixation device within a hole prepared in a bone.

The device 10 may be positioned on an inserter 30 which may assist an operator in positioning the device within a bone hole. The inserter 30 may include a distal end 31 on which the device 10 is positioned. The distal end 31 may be a blunt end, as illustrated in FIG. 4. Alternatively, the inserter distal end may be a forked end, such that the sleeve 11 nests within the fork, or may have an active clamping structure, similar to a forceps or the like, which can optionally engage or disengage the sleeve 11 as needed. Of course, the distal end 31 must have a sufficiently small size to maintain the usefulness of the small diameters of the fixation device, and the intended benefit of the device being implanted into a smaller diameter bone hole, particularly when the fixation device is to be implanted using an arthroscopic technique.

Furthermore, as illustrated in FIG. 4, this embodiment of fixation device may provide for better loading onto an inserter due to at least the relationship between the sleeve and the filament between openings 12*c* and 12*d*. Specifically, because the filament is outside the sleeve between these openings, the device may be more easily loaded onto the inserter because the sleeve and filament can be stacked atop one another. Additionally, for example, such a setup may allow the operator to prepare an even smaller tissue hole for implantation of the device 10 since the device, between openings 12*c* and 12*d*, has an even smaller diameter than, for example, other embodiments, such as for example the embodiment of FIGS. 5 and 6, where the filament 120 is inside the sleeve between openings 112*b* and 112*c*, such that the sleeve and filament are instead, effectively, a single larger structure.

As mentioned above, other embodiments of the fixation device may include a single sleeve having two or more filaments positioned within its interior. In one example of a sleeve having two filaments positioned therethrough, a first filament may, similar to filament 20 of FIG. 1, pass through the various openings of the sleeve. The second filament, however, may either also pass through the openings of the sleeve, or stay within the interior of the sleeve along the entire length of the sleeve. In a further example, where three sutures are positioned within a single sleeve, the first filament may pass through the sleeve, and openings, therein, as illustrated in FIG. 1. The second filament may either stay entirely within the interior of the sleeve along the length of the sleeve or may also pass through the openings of the sleeve, as in FIG. 1. The third filament may also either stay entirely within the interior of the sleeve along the length of the sleeve or may also pass through the openings of the sleeve, as in FIG. 1. Of course, further alternative arrangements are envisioned, including, for example, arrangements where one of the filaments only passes through a couple of the openings present in the sleeve.

In use, one embodiment of which is illustrated in FIGS. 1-3, the sleeve 11 may be used in a method of anchoring a filament 20 in a bone. Using a drill and drill guide (not shown), such as that found in U.S. application Ser. No. 12/821,504, filed Jun. 23, 2010, the entirety of which is incorporated by reference herein as if fully set forth herein, or other drill and drill guide known in the art, a drill hole 51 is prepared in bone 50 where it is desired to anchor a filament 20. The drill and drill guide may include a laser etching, or similar marking, or alternatively a hard stop between the drill and drill guide, to ensure proper drilling depth. For example, the hole may be prepared in the shoulder joint to repair labral tissue which has separated from the glenoid. The diameter of the hole may be, for example, about equal to the diameter of the sleeve itself, such that, the device, folded on itself, will compress and fit snuggly within the bone hole, even prior to deployment of the device, as will be discussed below. Thus, for example, for a 1.2 mm sleeve, the drill hole may have a diameter of about 1.2 mm, and for a 1.8 mm sleeve, the diameter of the drill hole may be about 1.8 mm Such matching of drill hole to device diameter may create a press-fit connection between the device the bone hole, providing initial contact between the device and the bone, prior to deployment of the device. The depth of the drill hole is dependent on the particular anatomy in which the device is to be implanted, but the depth may be, for example, typically between about 13-25 mm. In any event, the drill hole should pass through the cortical bone and enter into the cancellous bone 52. It should be noted that, if a straight guide, as is known in the art, is used, then these measurements should be used, depending on the size of the sleeve. However, if a curved guide is used, such as the above guide incorporated by reference, then the operator may, optionally, wish to make the bore hole slightly larger to ensure placement of the sleeve completely into the bore hole upon exiting the curved guide. As discussed below, upon deployment of the device, sufficient contact between the bone hole and the device may still be achieved to attain required pullout strength.

Once the hole is prepared, the drill is removed from the drill guide, and the drill guide may remain firmly in place at the bone hole. The device 10, positioned on an insertion tool 30, may then be passed through the drill guide (not shown) and to the hole in the bone, as illustrated in FIG. 4, for example. The sleeve 11 is then pressed into the bone hole, with the filament 20 positioned through the interior as illustrated, and may optionally be placed in the bone hole by lightly malleting using a mallet or like instrument to firmly seat the sleeve in the bone hole. Optionally, the inserter may have a laser etching, or other marking, which may assist the operator in accomplishing a proper insertion depth into the bone hole. At this point in the procedure, as illustrated in FIGS. 3A and 4, the device 10 is substantially folded in half within the bone hole, such that the two halves contact the bone hole side walls along a portion of their length. Such initial contact may achieve a press-fit engagement between the bone hole and the device such that the device is frictionally engaged by the bone hole which may provide initial friction to maintain the device within the bone hole, particularly, as below, when the inserter 30 is being removed from the bone hole. As in FIG. 3A, the fixation device may be placed as deeply as possible into the bone hole such that a portion of it may contact the floor of the bone hole. While not necessary, such placement may allow for maximum room for any potential upward migration of the fixation device within the bone hole.

Once the bone hole has been prepared, and the fixation device is positioned within the bone hole, the fixation device may then be deployed. As illustrated in FIGS. 3A and 3B, the inserter tool has been removed from the drill guide by pulling the inserter directly back through and out of the guide. The operator may then grasp the ends 21, 22 of the filament 20 which are extending from sleeve 11. Optionally, these filament ends may be removeably secured to the handle (not shown) of the inserter for ease of locating and for organizational benefits. The operator then may tension the ends of the filament 20, which may be accomplished with a single, continuous pull on the filament ends, to compress and set the sleeve 11 within the hole in the bone such that the sleeve compresses from its U-shape of FIG. 1 towards the W-shape of FIG. 2. Such compression occurs from the bottom of the U-shape upwards, as in FIGS. 3A-B, such that the bottom of the U-shape compresses towards the ends 13, 14 (although some downward compression of the ends 13, 14 towards the bottom of the U-shaped sleeve may also occur). Such compression may, as illustrated for example in FIG. 3A, lift the sleeve 11 from the floor of the bone hole. Further tensioning on the filament ends 21, 22 may result, as illustrated in FIG. 3C, in migration of the fixation device 10 proximally within the bone hole and towards the cortical bone 50. Such proximal migration of the fixation device may result in even further compression of the sleeve 11 as well as additional frictional engagement with the bone hole walls. In a further example, the sleeve 11 may migrate proximally until it contacts the underside of the cortical bone layer 50, such that the sleeve 11 may be prevented from further movement, e.g., out of the bone hole, by its engagement against the underside of the cortical bone layer. Such engagement may create additional resistance against pullout.

The operator may then verify that the sleeve 11 is set in the bone hole, by performing a tug on the filament ends 21, 22, and may additionally verify that the filament 20 can still slide through the sleeve 11 by pulling on one of the ends 21, 22. The filament 20 should still be slidable through sleeve 11, even when the sleeve is compressed, in order to perform manipulation of the filament 20 in order to, for example, gather and/or pierce tissue to thereby secure tissue to, or adjacent to, the implantation site. For example, such ability to manipulate the filament after deployment of the sleeve is important in rotator cuff surgery as the filament must be manipulable to properly reattach the cuff tissue back to or adjacent to the implantation site.

Alternatively, when tensioning the filament ends 21, 22, rather than pulling both ends simultaneously until the device is completely deployed, the operator, while holding both ends to prevent sliding of the filament, may instead pull on the ends sequentially, such that first, one of the ends 21 or 22 is pulled, and subsequently, the other of the ends 22 or 21 is pulled, to deploy the device.

In another alternative, where the filament includes indicating markers 17*a-d*, the operator may use such markers as a guide in confirming proper deployment has occurred. As illustrated in FIGS. 1 and 2, markers 17*a-d* are initially positioned along the length of the sleeve, prior to deployment. As the filament ends 21, 22 are pulled, to deploy the device, the markers 17*a-d* are pulled proximally, towards the operator, along with the filament ends. As illustrated, the sleeve 11 may also migrate proximally during this step. As the proximal markers 17*a*, 17*d* pass above the cortical bone 50, they may indicate to the operator that the device has properly deployed. The operator may continue to pull on the ends of the filament until fully deployed (e.g., the filament does not move proximally any further using typical pulling force on the filament ends). However, upon this subsequent pulling, if the distal markers 17*b*, 17*c* are exposed above the cortical bone surface 50, then they may indicate that the implant is very close to being pulled out of the bone and the operator should decide if the resistance they feel is adequate or if they would prefer to pull the implant out completely and attempt the procedure again.

In any event, as the filament ends are pulled and the device is deployed, the sleeve resists pullout from the bore hole due to the friction against the cancellous bone 52 surrounding bone hole 51, and such friction is increased as the sleeve is compressed further, as well as if the sleeve migrates proximally (and particularly if the sleeve contacts the underside of the cortical bone layer). Moreover, as the sleeve is compressed, the forces applied to the sleeve may also be transferred to the surrounding cancellous bone, as illustrated in FIGS. 3B-C. Such affect on the cancellous bone may create additional friction and thus anchorage for the sleeve in the bone hole, to resist potential pullout. Further, as the device compresses and further engages the walls of bone hole 51, the surrounding cancellous bone 52 may interdigitate with at least a portion of the sleeve to provide added anchorage of the device within the bone hole. Such interdigitation may include, for example, cancellous bone protrusions overlapping and/or passing between the filaments of the sleeve to engage the sleeve. Moreover, the compressed sleeve, as discussed above, may migrate and engage the underside of the cortical surface, and may through such migration compress even further, and in this more compressed shape will result in a very strong structure to resist being pulled out the small hole in the cortical bone, as illustrated in FIG. 3C.

In another alternative of this method, the insertion tool 30 may also remain within the bone hole during deployment (not shown), to assist in maintaining the sleeve within the bone hole as the filament ends are pulled and the sleeve is compressed.

Following deployment of the device 10, with the sleeve 11 and filament 20 fixedly secured within the bone hole, the device may achieve pullout strengths comparable to traditional metal and polymeric devices despite this device 10 being constructed solely of suture or like filament material. For example, the embodiment of FIGS. 1-4, utilizing #2 suture in a foam block, achieved pullout strengths of at least 60 lbf, though higher pullout strengths are likely depending on the strength of the underlying bone, the diameter of filament 20, and other such variables. Similarly, using the embodiment of FIGS. 1-4, with the addition of a second filament 20, of #2 suture, woven through sleeve 11, a pullout strength of at least 65 lbf was recorded prior to the test foam block fracturing.

In accordance with this embodiment of a method of use, the sleeve 11 is anchored in bone, thus securing the filament 20 to the bone, while still allowing the filament to be slidable through the sleeve. Such ability to maintain the filament in a sliding association to the sleeve, even after the sleeve has been compressed, is important in shoulder and hip surgery, among other surgeries, because the operator may require an adjustable suture length to secure soft tissue at the repair site adjacent to the hole in the bone. This is especially important in arthroscopic surgery because sliding knots are frequently used to secure tissue that is accessed through a cannula. Such sliding association is maintained at least in part by the setup of the filament relative to the sleeve in that the filament passes through the sleeve only once and in a single direction. For example, the filament enters from one end of the sleeve, passes in and out of the plurality of openings in sequential order along the length of the sleeve, and then exits out the second end of the sleeve. Thus, as the sleeve compresses to form a W-shape, as in FIG. 2, the various openings in the sleeve tend to align adjacent one another such that the filament maintains, substantially, a U-shape, and thus can slide through the ends and the openings along the length of the sleeve regardless of the shape of the sleeve.

In one example of the device 10 of FIGS. 1-4, the force required to slide the suture through the deployed sleeve was measured, following a deployment force, applied by tensioning of the ends of the filament, of about 12 lbs. Once the sleeve was deployed (e.g., in the W-shape), between about 1.75-2.75 lbf was required to slide the filament through the sleeve. Of course, alternative embodiments of filaments and sleeves may result in different sliding forces needed to manipulate the filament through the sleeve.

The present invention may also be used, in another embodiment, in a method of securing a tissue to a bone. After the filament has been tensioned and the sleeve anchored in the bone, as in the above embodiment of the method of securing a filament to bone, the filament may then be used to secure tissue to a reattachment site located on the bone at or adjacent to the bone hole. In one embodiment, the filament may be used to reattach rotator cuff tissue, and thus the filament may be manipulated to engage and/or collect the cuff tissue and may be tied or otherwise secured to hold the tissue at the reattachment site. For example, one end 21 or 22 of the filament may be pulled through the tissue (using a needle or the like) and be used to pull the tissue to the reattachment site at or adjacent to the bone hole, at which point the other end of the filament may be incorporated to tie the tissue to the reattachment site, or the like. Other potential tissues on which this method may be used includes at least a portion of a shoulder labrum, at least a portion of a hip labrum, or the like.

In a further embodiment, the fixation device of the present invention may be used in a method of repair of soft tissue, such as a meniscus, ligament or tendon, or the like, wherein such methods do not require that the device 10 be deployed within a bone hole 51. Instead, the device, as to these methods, would function similar to a button anchor for use in, for example, ACL repair, such as is disclosed in U.S. patent application Ser. No. 12/682,324, now U.S. Published App. No. 2011/0125189, filed Oct. 9, 2008 and assigned to the same assignee as this application, the entirety of which is incorporated by reference herein as if fully set forth herein. The device may also serve as a button anchor for use in, for example, meniscus or cartilage repair, such as is disclosed in U.S. patent application Ser. No. 12/550,069, now U.S. Published App. No. 2009/0312792, filed Aug. 28, 2009, the entirety of which is incorporated by reference herein as if fully set forth herein.

In terms of, for example, a ligament or tendon repair, such as an ACL repair, where a tissue graft is secured within a bone tunnel, the device 10 may, following preparation of the bone tunnel by known means, be passed up through the tunnel, using an inserter such as inserter 30. In this embodiment, at least the distal-most portion of the tunnel (e.g., the lateral side of a femur) may have a diameter which allows the undeployed device, as illustrated in FIG. 1, to pass through the tunnel but not the deployed device, as illustrated in FIG. 2. Once the device exits from the bone tunnel, and is thus positioned on the lateral side of the bone (e.g., femur), the filament ends 21, 22, which remain outside the opposite end of the bone tunnel, may be pulled to deploy the anchor. The deployment of the anchor may compress the sleeve 11 in a manner, as in FIG. 2, which inhibits the sleeve from passing back through the tunnel. The filament ends may then be tied or otherwise maneuvered to engage the ACL graft, which may then be placed within the bone tunnel as is known in the art. Thus, the device 10 may act as an anchor against which a graft may be tensioned to complete the repair.

In terms of, for example, the repair of a soft tissue tear such as in a meniscus or cartilage mass, where the tear is to be approximated to promote healing of same, the device 10 may be passed through the tissue mass, through the tear, and through a side surface of the tissue. In this embodiment, the inserter 30 may include, for example, a needle tip or other structure capable of forming a pathway through which the device, in the undeployed configuration as in FIG. 1, may pass. Once the device is positioned outside the side surface of the tissue, the filament ends, which remain in position on the opposite side of the tissue, may be pulled to deploy the sleeve 11. Once the sleeve is deployed, the sleeve is thus too wide to fit back through the pathway. The filament ends may then be tied or otherwise maneuvered to approximate the tear, which is positioned between the sleeve and the filament ends. The filament ends may then form a knot, or otherwise secure to one another, against the opposite side of the tissue. Thus, the device 10 may act as an anchor against which the filament ends may be tensioned to approximate the tear in the soft tissue to complete the repair.

Alternatively, these methods may also be used to secure a bone to hard tissue, such as another bone, as in a syndesmosis repair. In such a method, the filament may, as above, pass through the other bone (e.g., through a bone through-hole) or may pass around the other bone to effect a reattachment of the two bones to one another to promote healing of the injured joint. Thus, upon activation of the device, the filament ends may then engage the other bone and be tied together to secure the two bones together. Such methods of use may be utilized in the repair of bone in the ankle joint or in the acromioclavicular joint.

Figure 5:
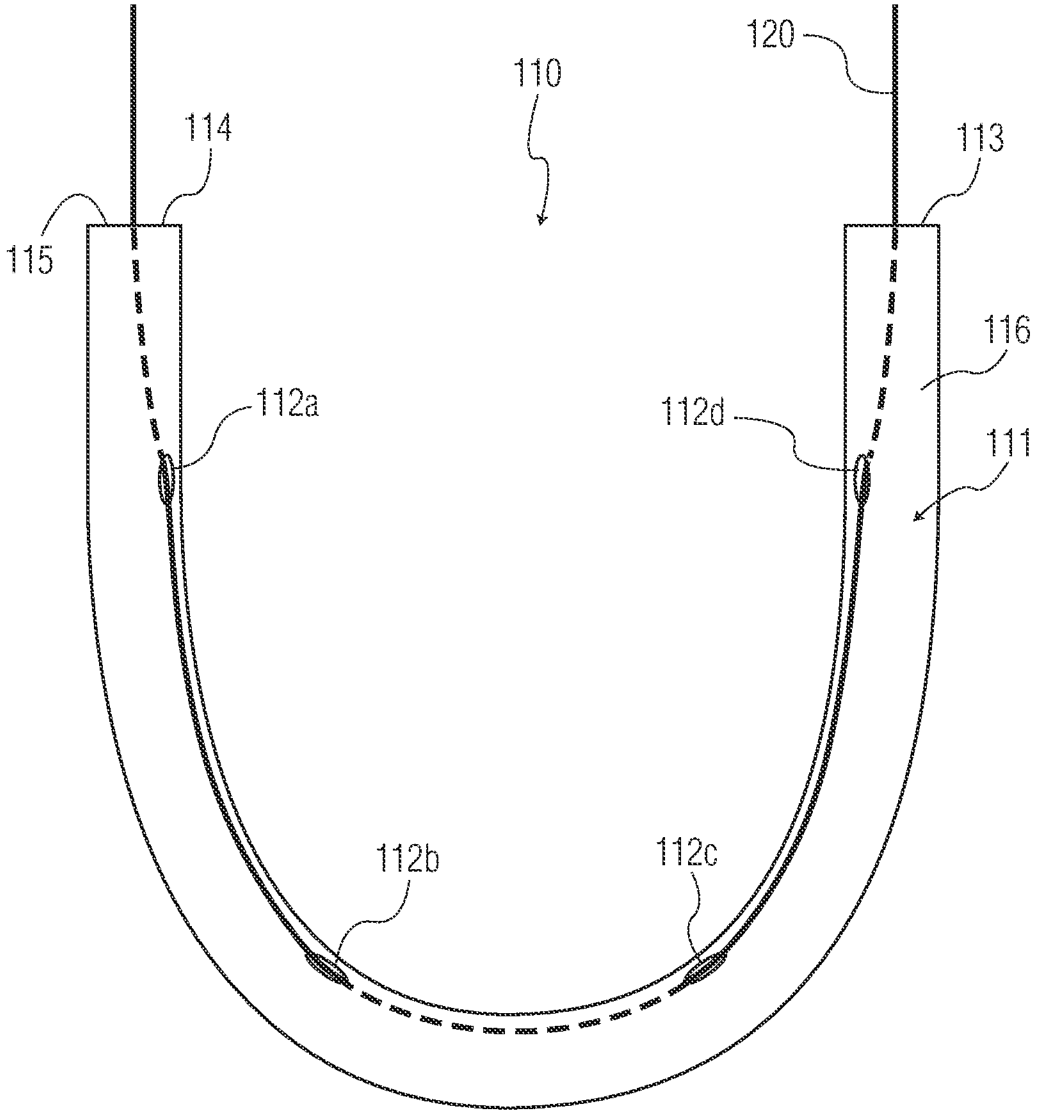
FIG. 5 illustrates another embodiment of a fixation device of the present invention.
Figure 6:
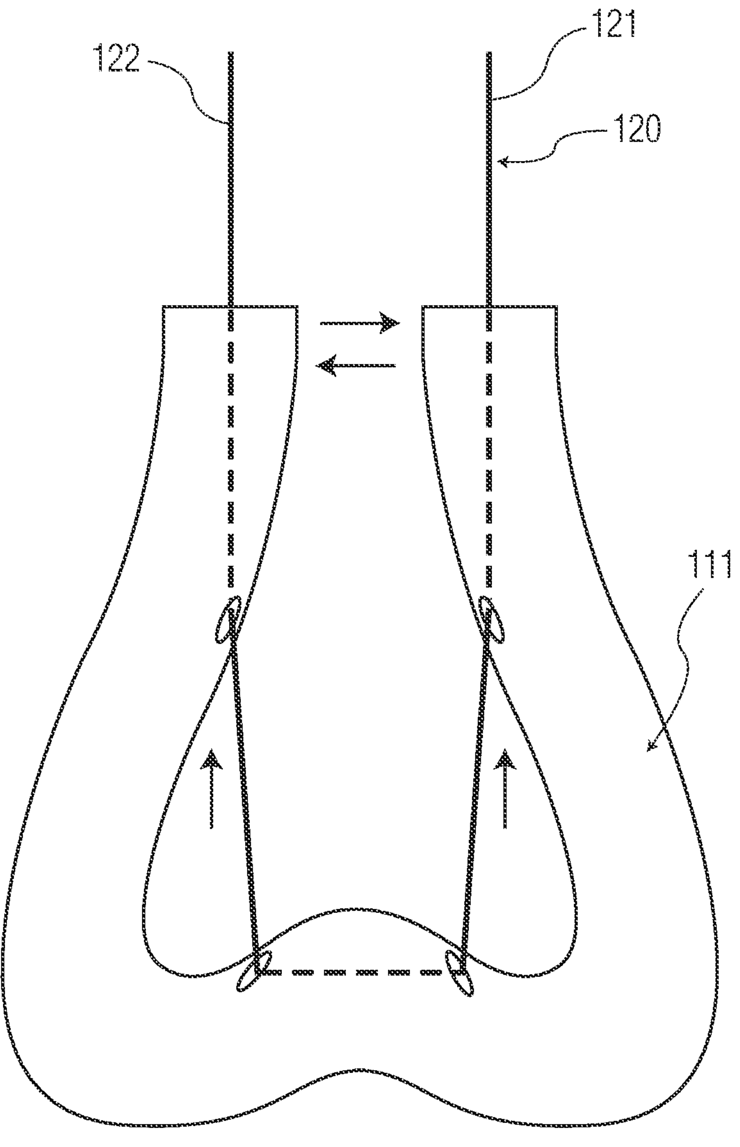
FIG. 6 illustrates the fixation device of FIG. 5 after tensioning the filament 120.

As illustrated in FIGS. 5 and 6, another embodiment of fixation device 110 includes a sleeve member 111 and a filament 120. The sleeve member 111 includes an interior 115 and an exterior surface 116, both of which extend along a length defined between a first end 113 and a second end 114. The sleeve member 111 may be substantially hollow. The exterior surface also includes at least two openings 112*b*, 112*c* positioned along the length of the exterior surface 116, each of which form a passageway through the exterior surface and into the interior 115. As illustrated, in this embodiment, the exterior surface may include four openings (for example, 12*a*, 12*b*, 12*c*, 12*d*), though any other number of openings in any configuration along the length of the exterior surface may be present.

This embodiment also includes a filament 120 having a length and at least a portion of this length is positioned within the interior 115 of sleeve 111. The filament is slidable within the interior 115. The filament may also pass through at least one of the openings 112 along the exterior surface 116 of the sleeve 111. For example, as in FIG. 5, filament 120 may exit the interior 115 through opening 112*a* re-enter the interior through opening 112*b*, exit the interior once again through opening 112*c*, and re-enter the interior through opening 112*d*.

Comparing FIG. 5 with the first disclosed embodiment, in FIG. 1, it is apparent that the filament 120 remains inside the interior at the bottom portion (between openings 112*b* and 112*c*), while the filament 20 is outside of the interior at the similar bottom portion (between openings 12*c* and 12*d*) in FIG. 1. In addition to the aforementioned differences in width of the device upon placement on an inserter, these differing configurations may provide different forces on the sleeve as the filament 20, 120 is tensioned to compress the sleeve. For example, in FIG. 1, as the filament 20 is tensioned, openings 12*c* and 12*d* may be pulled towards one another such that the sleeve between these openings may be pinched or crushed to form the W-shape. In FIG. 5, however, the tensioning of filament 120 may provide an upward force at openings 112*b* and 112*c*, thereby moving the portion of the sleeve between these openings up towards the first and second ends 113, 114 which may form the W-shape. Thus, these two exemplary embodiments illustrate two different relationships of a sleeve and a filament, either of which may result in a compressed sleeve capable of securing a filament within a bone hole.

The fixation device embodiment illustrated in FIGS. 5 and 6 may be used in similar methods of use as illustrated in FIGS. 3 and 4 and as discussed above.

Figure 7A:
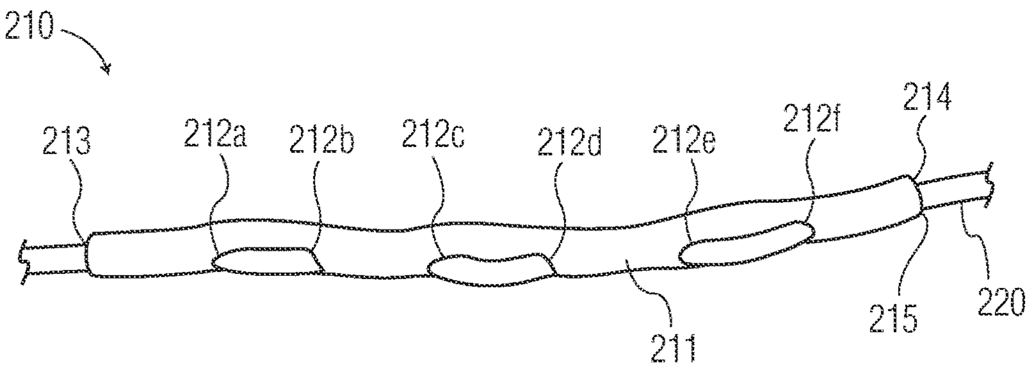
FIGS. 7A-C illustrate a further embodiment of a fixation device of the present invention.
Figure 7B:
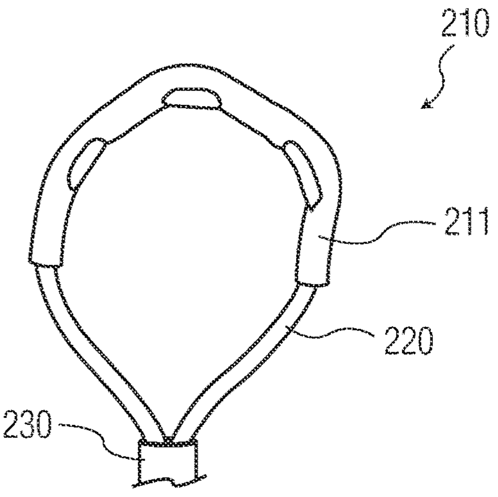
Figure 7C:
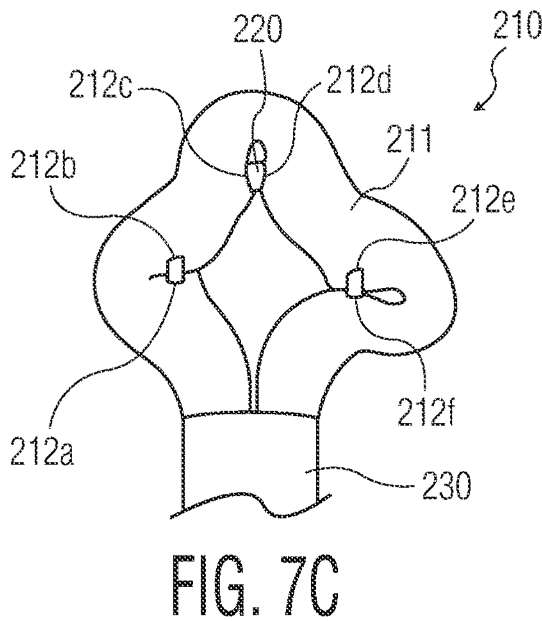

In further alternative embodiments, which also may be used in similar methods of use as illustrated in FIGS. 3 and 4 and as discussed above, the sleeve and filament may have a relationship which results in the sleeve, upon compressing, attaining a compressed shape other than the W-shape discussed above. For example, as illustrated in FIGS. 7A-C, the sleeve 211 may have a U-shaped starting shape (FIG. 7B), but upon compressing, may attain a clover shape (FIG. 7C). Similar to the embodiments discussed in detail above, the openings 212*a-f* of this embodiment likewise, upon compression, may move towards one another, e.g., opening 212*a* and opening 212*b* are adjacent one another, and even contacting one another, upon compression of sleeve 211. Moreover, in this closer shape, the filament 220 may still have a generally U-shaped arrangement, within the clover shape of sleeve 211, such that the filament 220 may still slide within the sleeve 211.

FIGS. 8-16 illustrate other exemplary shapes which the sleeve may attain upon compressing. As illustrated, the various shapes depend on a variety of factors including but not limited to the number of openings along the length of the sleeve, the location of the openings along the sleeve, the relationship of the filament relative to the sleeve, and the shape of the openings on the sleeve. The pullout strength and capability of being used in the above disclosed methods may be similar to the embodiment disclosed in FIGS. 1-4. It should be noted that in all of the embodiments disclosed in this application, particularly those in FIGS. 7-16, upon compression, the sleeve may not always attain the same shape each and every time. For example, the shape and size of the bone hole may force the sleeve into a different shape, upon compression, than those illustrated herein. Also, in another example, the exact dimensions and locations of the openings through the sleeve may be altered slightly which could result in an alternative shape of the sleeve upon its compression.

Figure 8A:
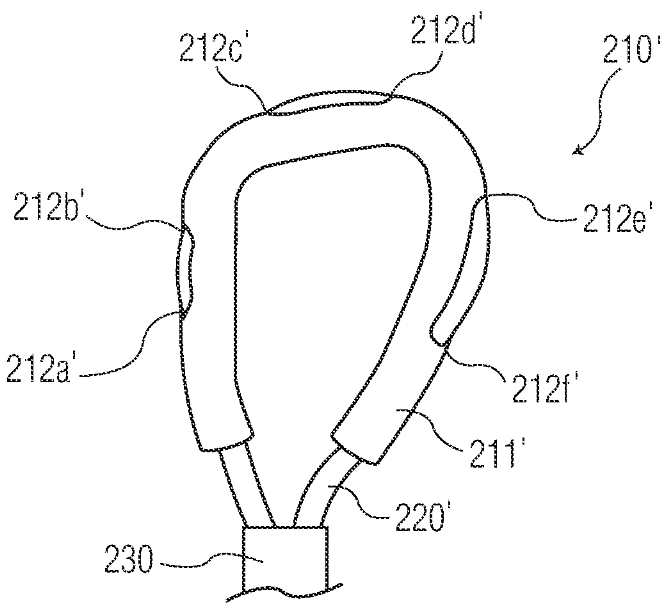
FIGS. 8A-B illustrate an alternative configuration of the fixation device of FIGS. 7A-C.
Figure 8B:
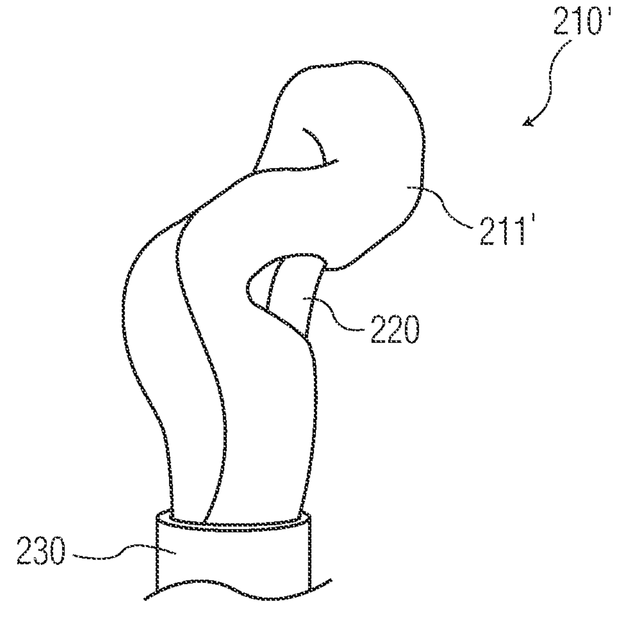

For example, in FIGS. 8A-B, the relationship of the sleeve 211' and filament 220' is the same as the relationship illustrated in FIG. 7A, except that when the device 210' is curved into the U-shape of FIG. 8A, the filament 220' exits outside the sleeve 211' on the outside of the U-shape, e.g., between openings 212*a*' and 212*b*'. By contrast, the filament 220 illustrated in FIG. 7B, upon exiting the sleeve 211, exits on the inside of the U-shape, e.g., between openings 212*a* and 212*b*. While FIGS. 7B and 8A appear to be quite similar, the two different relationships may result in drastic differences once the sleeves are compressed, as illustrated in FIGS. 7C and 8B, which illustrate alternative shapes of compressed sleeves.

Figure 9A:
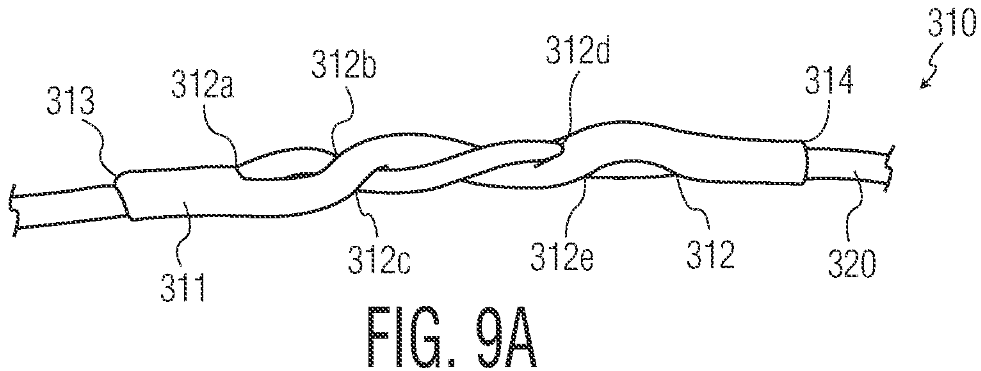
FIGS. 9A-C illustrate yet another embodiment of a fixation device of the present invention.
Figure 9B:
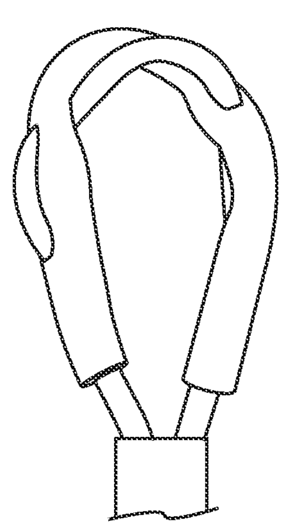
Figure 9C:
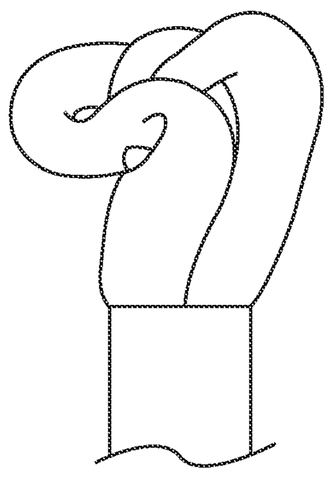
Figure 11A:
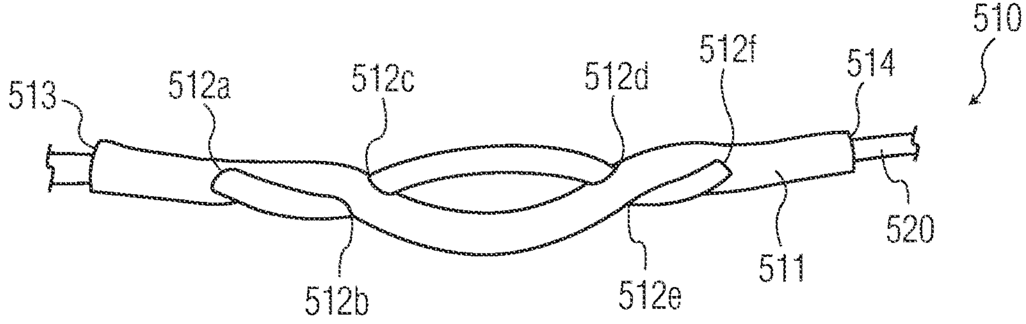
FIGS. 11A-C illustrate a further embodiment of a fixation device of the present invention.
Figure 11B:
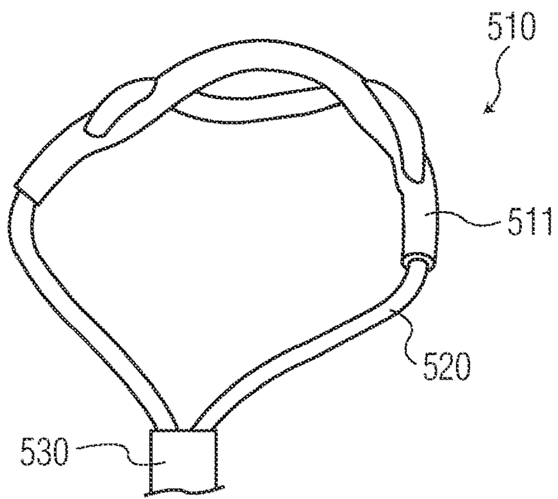
Figure 11C:
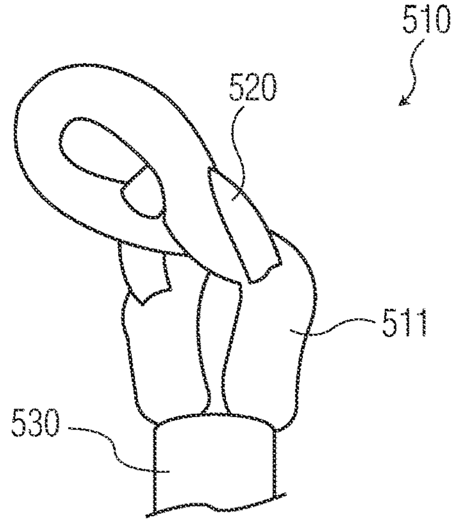
Figure 12A:
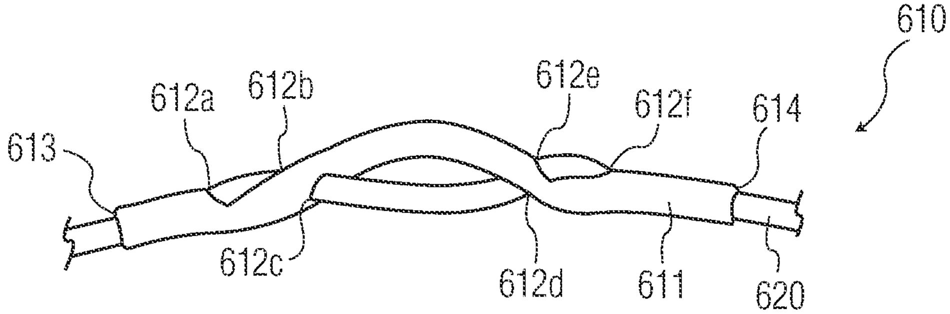
FIGS. 12A-C illustrate an additional embodiment of a fixation device of the present invention.
Figure 12B:
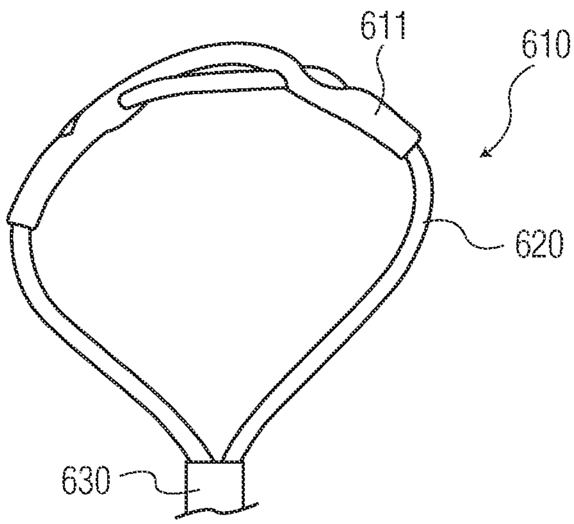
Figure 12C:
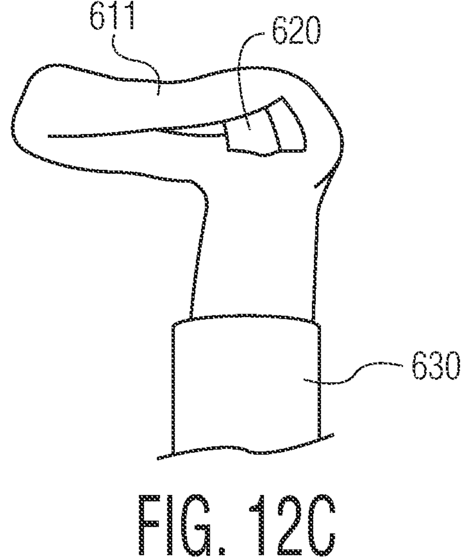

In yet another example of such differences, FIGS. 9A-C illustrate another alternative embodiment of a relationship of a sleeve 311 and a filament 320 forming an device 310. In this embodiment, openings 312*a* and 312*b* are radially offset from one another, and the filament 320 must be twisted around the outside of the sleeve to reach between opening 312*a* and opening 312*b*. Upon folding of the sleeve 311 (FIG. 9B), the openings 312*a* and 312*b* remain radially offset to one another, and filament 320 twists around sleeve 311 such that it may pass through the openings 312*a* and 312*b*. Such a relationship may result in yet another alternative shape of the sleeve upon compressing during deployment of the sleeve. Again, it should be observed, that the filament, upon compression of the sleeve, substantially maintains a U-shape, within and around the sleeve, such that sliding of the filament remains possible.

In some embodiments, as in FIGS. 1-8, the filament, when positioned within the interior of the sleeve, may extend in a generally longitudinal path along the length of the sleeve such that the filament and sleeve are substantially parallel with one another. Using FIG. 7A as an example, filament 220 is generally positioned axially along the length of the sleeve 211 while entering and exiting the interior of the sleeve via openings 212 which are positioned along the length of sleeve 211 and generally in series—one after the other—along the length.

In an alternative example, however, the filament may be generally transverse to the interior of the sleeve, when the filament is positioned within the interior. For example, such a relationship is variously illustrated in FIGS. 9-16. As illustrated clearly in FIGS. 14A-C, for example, the filament may pass through opening 812*b*, travel transversely through the interior, and out opening 812*c*. Such a relationship of the filament and sleeve is also shown as to openings 812*d* and 812*e*, and 812*f* and 812*g*. As shown, however, the filament may still remain substantially parallel to the interior of the sleeve at the ends of the sleeve, e.g., between end 813 and opening 812*a* and end 814 and opening 812*h*, such that the filament exits from the interior at the first and second ends. This is similar to other embodiments herein. Such a relationship may provide for better sliding of the filament through the sleeve.

Such embodiments having a generally transverse configuration when the filament passes through the sleeve as FIGS. 9-16 may result in alternative shapes of the sleeve when compressed. As in the other embodiments described above, the shape of the sleeve when compressed will depend on the number of openings along the length of the sleeve, the location of the openings along the sleeve, the relationship of the filament relative to the sleeve, and the shape of the openings on the sleeve.

Figure 13A:
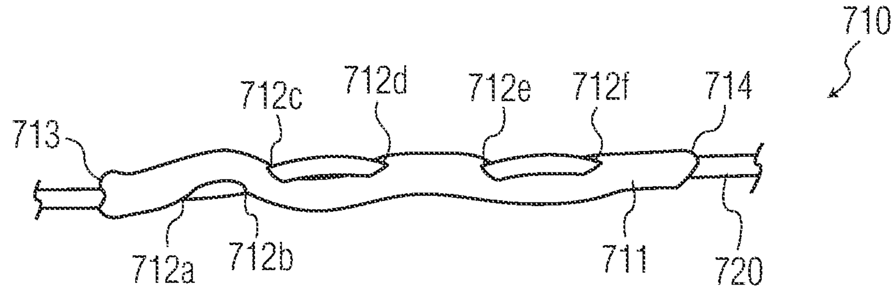
FIGS. 13A-C illustrate yet another embodiment of a fixation device of the present invention.
Figure 13B:
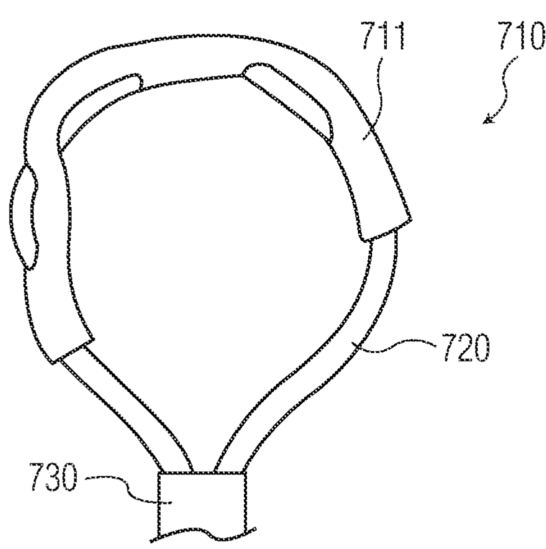
Figure 13C:
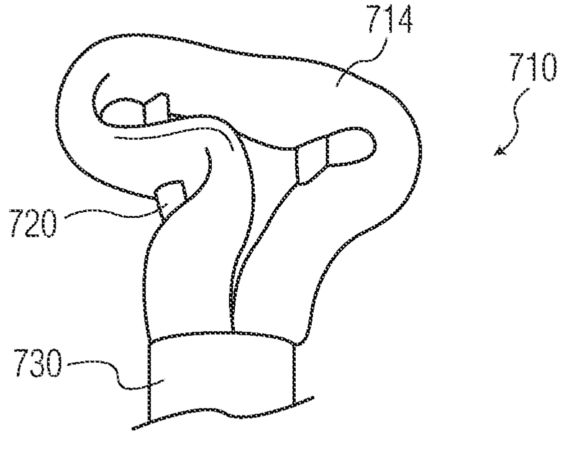

In yet another alternative, the filament and sleeve may be in a hybrid configuration whereby the filament, along at least a first portion of its length other than at the ends of the sleeve, is substantially parallel to the interior of the sleeve, and along at least one other portion, may be generally transverse to the interior of the sleeve. Such variations are illustrated in FIGS. 13A-C. Thus, in this type of relationship, the filament is again generally parallel to the sleeve at the ends of the sleeve (between end 713 and opening 712*a* and end 714 and opening 712*f*). The filament and sleeve are also generally parallel between opening 712*c* through openings 712*d* and 712*e* and on to opening 712*f* and end 714. The filament is transverse to the sleeve from opening 712*b* to 712*c*.

The various embodiments illustrated in the figures provide many examples of the device of the present invention. While the relationship between the filament and sleeve varies from embodiment to embodiment, each of the embodiments have similarities such as, for example: the filament and sleeve are generally parallel to one another at the ends of the sleeve such that the filament exits from the ends of the sleeve; the sleeve and filament can be moved to a U-shape, prior to deployment of the device, and loaded onto an inserter; and with the sleeve compressed, the filament generally maintains a U-shape such that it may remain slidable through the sleeve even when the sleeve is compressed.

These various embodiments result in a smaller device than those presently in public use because the filament only passes through the interior of the sleeve once along its length, remains within the sleeve and exiting through the ends of the sleeve, and, in many embodiments, is outside the sleeve at the location where the inserter tip holds the device, resulting in a generally smaller diameter of the device. The smaller sized device allows for a smaller hole to be prepared in the bone, and a smaller access port to the bone, which results in a smaller surgical site in the patient.

Moreover, in the event the device does pull out from the bone post-surgery, since the device is made entirely of a filament-like material, such as suture, the device would not lacerate adjacent anatomy within the patient, which is a concern if a traditional device pulls out from the bone.

The present invention may also include various kits and systems which include at least one of the device embodiments above. For example, in one embodiment, the present invention may include a system including a device, including a sleeve and filament, and an inserter. The system may be packaged individually, and even sold separately, such that the surgeon may place the device on the inserter. Alternatively, the device may come pre-installed on the inserter, within a single package, such that the surgeon may remove the system from the packaging and immediately use the system and install the device within a bone hole.

In another embodiment, such a system may further include the aforementioned drill guide and drill, which may come pre-packaged as an entire system or which may be sold separately and later combined by the surgeon and used for the above discussed methods of use.

In another embodiment, the present invention may include a kit which includes a plurality of devices, each having a sleeve and filament, and an inserter. The plurality of devices may be any combination of the above devices. For example, the plurality of devices may include more than one of the device disclosed in FIGS. 1-4, wherein the sleeve of each device has a different diameter and/or length than the other sleeves of the other devices. Alternatively, the sleeve of each device may have a different number and/or positioning of openings, such that the appropriate device may be selected which will provide the desired pullout strength or compression properties (which may be dependent on the anatomy in which the device is implanted, the condition of the bone in which the device is implanted, or the like). Alternatively, the plurality of devices may include various devices of the above embodiments, or other similar devices, from which a surgeon may select from based on the specifics of the surgical site, pullout strength required, and the like.

Such kits may further include a plurality of drill bits which may be matched with a device, selected from the plurality of devices, to prepare an appropriately sized bone hole for insertion of the device.

Any other suitable combination is also envisioned for the above systems and kits which may be useful or desirable to a surgeon. For example, the various components of the systems or kits may all be available to a surgeon a la carte, such that a unique system or kit may be created for a particular surgeon dependent on the needs or desires of the particular surgeon.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A filamentary fixation system, comprising:

a sleeve formed of filamentary material having a length and a lumen defined therethrough, the sleeve defining, in order along the length of the sleeve, first, second, third, and fourth openings, and a bottom portion configured to engage an inserter for inserting the sleeve into a bone hole through a cortical bone layer and into cancellous bone, the bottom portion being located between the second and third openings; and a filament formed of filamentary material including a first free end and a second free end, the filament being disposed entirely outside the sleeve from the first opening to the second opening, entirely inside the lumen of the sleeve from the second opening to the third opening, and entirely outside the sleeve from the third opening to the fourth opening, wherein the filament does not overlap itself along the length of the sleeve and the first free end and second free end are configured to be tensioned in a direction away from the bone hole to compress the bottom portion in a direction towards the cortical bone layer.

2. The filamentary fixation system of claim 1, wherein a diameter of the lumen is larger than a diameter of the filament such that the filament is slidable within the lumen.

3. The filamentary fixation system of claim 1, wherein the sleeve includes an inner surface defining the lumen and an exterior surface, and the first, second, third, and fourth openings extend entirely through the sleeve from the exterior surface to the lumen.

4. The filamentary fixation system of claim 3, wherein the filament exits the lumen through the first opening, enters the lumen through the second opening, exits the lumen through the third opening, and enters the lumen through the fourth opening.

5. The filamentary fixation system of claim 1, wherein the filament is positioned entirely within the lumen of the sleeve within the bottom portion.

6. The filamentary fixation system of claim 1, wherein the first free end and second free end are configured to be tensioned to pinch the second opening and the third opening together and compresses the bottom portion upwards such that at least a portion of the sleeve forms a W-shape.

7. The filamentary fixation system of claim 1, wherein the filament includes at least one indicating marker along a length of the filament.

8. The filamentary fixation system of claim 1, further comprising the inserter having a distal end provided with a forked tip.

9. The filamentary fixation system of claim 8, wherein the forked tip is positioned at a distal-most end of the inserter, wherein the bottom portion of the sleeve is configured to engage the forked tip.

10. A filamentary fixation kit, comprising:

a sleeve formed of filamentary material having a length, an exterior surface and an interior surface defining a lumen extending through the sleeve, the sleeve defining, in order along the length of the sleeve, first, second, third, and fourth openings, and a bottom portion configured to engage an inserter for inserting the sleeve into a bone hole through a cortical bone layer and into cancellous bone, the bottom portion being located between the second and third openings; and a filament formed of filamentary material including a first free end and a second free end, the filament being disposed entirely outside the sleeve from the first opening to the second opening, entirely inside the lumen of the sleeve from the second opening to the third opening, and entirely outside the sleeve from the third opening to the fourth opening such that the filament does not overlap itself along the length of the sleeve, wherein the first free end and second free end are configured to be tensioned in a direction away from the bone hole to compress the bottom portion in a direction towards the cortical bone layer; and the inserter having a distal end for engaging the bottom portion of the sleeve.

11. The filamentary fixation kit of claim 10, wherein the distal end of the inserter comprises a forked tip.

12. A surgical method, comprising the steps of:

accessing bone and preparing a bone hole through a cortical bone layer and into cancellous bone;

obtaining a fixation device, the fixation device, including:

a sleeve formed of filamentary material having a lumen defined therethrough, the sleeve defining, in order along the length of the sleeve, first, second, third, and fourth openings, and a bottom portion located between the second and third openings;

a filament formed of filamentary material including a first free end and a second free end, the filament being disposed entirely outside the sleeve from the first opening to the second opening, entirely inside the lumen of the sleeve from the second opening to the third opening, and entirely outside the sleeve from the third opening to the fourth opening such that the filament does not overlap itself along the length of the sleeve;

an inserter positioned against the bottom portion of the sleeve in between the second opening and the third opening;

inserting the fixation device into the bone hole using the inserter; and tensioning the first free end and the second free end in a direction away from the bone hole to compress the bottom portion in a direction towards the cortical bone layer.

13. The surgical method of claim 12, wherein the tensioning step comprises sliding the filament though the sleeve.

14. The surgical method of claim 12, wherein the tensioning step comprises tensioning the first and second free ends of the filament such that the second and third openings are pinched, and the bottom portion moves upwards.

15. The surgical method of claim 12, wherein the filament further comprises at least one indicating marker, and during the tensioning step, at least a portion of the at least one indicating marker slides relative to the sleeve from a position beneath a surface of the bone hole to a position above the surface of the bone hole.

16. The surgical method of claim 12, wherein the preparing the bone hole step comprises drilling the bone hole to a diameter of between about 1.2 mm and 1.8 mm.

17. The surgical method of claim 12, wherein the obtaining step comprises a forked end of the inserter adapted to be engaged against the bottom portion of the sleeve.

18. The surgical method of claim 12, wherein the inserting step comprises engaging the bottom portion of the sleeve against a floor of the bone hole.

19. The surgical method of claim 12, wherein the tensioning step comprises tensioning the first and second free ends of the filament to compress at least a portion of the sleeve into a W-shape.

20. The surgical method of claim 12, wherein the surgical method comprises repairing soft tissue of a rotator cuff, a shoulder labrum, or a hip labrum.

* * * * *